US012721875B2

(12) United States Patent
Shi et al.

(10) Patent No.: US 12,721,875 B2
(45) Date of Patent: Sep. 1, 2026

(54) DRUG FOR TREATMENT OF BREAST CANCER WITH ANTLER AND GINSENG AS SOVEREIGN DRUG AND PREPARATION METHOD AND APPLICATION THEREOF

(71) Applicant: Jilin University, Changchun (CN)

(72) Inventors: Aiping Shi, Changchun (CN); Wenfeng Zhang, Changchun (CN); Jingdong Xu, Changchun (CN)

( * ) Notice: Subject to any disclaimer, the term of this patent is extended or adjusted under 35 U.S.C. 154(b) by 0 days.

(21) Appl. No.: 19/055,569

(22) Filed: Feb. 18, 2025

(65) Prior Publication Data

US 2025/0281559 A1 Sep. 11, 2025

(30) Foreign Application Priority Data

Mar. 10, 2024 (CN) ......................... 202410268338.9

(51) Int. Cl.

| | |
|---|---|
| ***A61K 36/00*** | (2006.01) |
| ***A61K 9/16*** | (2006.01) |
| ***A61K 35/32*** | (2015.01) |
| ***A61K 36/232*** | (2006.01) |
| ***A61K 36/233*** | (2006.01) |
| ***A61K 36/258*** | (2006.01) |
| ***A61K 36/539*** | (2006.01) |
| ***A61K 36/65*** | (2006.01) |
| ***A61K 36/8905*** | (2006.01) |
| ***A61K 36/8966*** | (2006.01) |
| ***A61P 35/00*** | (2006.01) |

(52) U.S. Cl.

CPC .......... *A61K 36/258* (2013.01); *A61K 9/1682* (2013.01); *A61K 35/32* (2013.01); *A61K 36/232* (2013.01); *A61K 36/233* (2013.01); *A61K 36/539* (2013.01); *A61K 36/65* (2013.01); *A61K 36/8905* (2013.01); *A61K 36/8966* (2013.01); *A61P 35/00* (2018.01)

(58) Field of Classification Search

CPC .................................................... A61K 36/258

See application file for complete search history.

*Primary Examiner* — Qiuwen Mi

(57) ABSTRACT

A drug for treatment of breast cancer with antler and ginseng as sovereign drug and preparation method and application thereof are disclosed, where the drug is made of 12 parts of antler and 3 parts of ginseng as the sovereign drug, 10 parts of *Angelicae sinensis radix* and 10 parts of *Radix paeoniae alba* as the adjuvant drug, and combined with 5 parts of *Radix bupleuri*, 5 parts of *Scutellariae radix*, 10 parts of *Cyperi rhizoma* and 10 parts of thunberg fritillary bulb; the preparation method includes: step 1, soaking antler and ginseng separately; step 2, taking *Angelicae sinensis radix, Radix paeoniae alba, Radix bupleuri, Scutellariae radix, Cyperi rhizoma* and thunberg fritillary and adding water to fully immerse; step 3, decocting; step 4, filtering by gauze and combining filtrate for 3 times; and step 5, compressing to a paste, freezing and drying, and sealing and storing for future use.

2 Claims, 17 Drawing Sheets

DRUG FOR TREATMENT OF BREAST CANCER WITH ANTLER AND GINSENG AS SOVEREIGN DRUG AND PREPARATION METHOD AND APPLICATION THEREOF

CROSS REFERENCE TO THE RELATED APPLICATIONS

This application is based upon and claims priority to Chinese Patent Application No. 202410268338.9, filed on Mar. 10, 2024, the entire contents of which are incorporated herein by reference.

TECHNICAL FIELD

The present invention relates to a drug and preparation method and application thereof, in particular to a drug for a treatment of breast cancer with antler and ginseng as a sovereign drug and preparation method and application thereof.

BACKGROUND

At present, the statistics from the relevant organizations indicate that the incidence of breast cancer has become the number one female malignant tumor in the world. The current mainstream treatment of breast cancer includes chemotherapy, endocrine, targeted, immune therapy, and other Modern medicine-based treatments. However, Modern medicine has two problems: firstly, Modern medicine has high side effects, the patient is difficult to tolerate, the compliance is poor, and the patient's own immunity is decreased due to the treatment and tumor, thereby affecting the therapeutic outcome. Endocrine therapy is the smallest side effect modern medicine comparing with the others, but only 60% of patients can complete the treatment, and most patients will have recurrence and metastasis due to discontinuation of treatment.

Mechanism of Modern medicine is to kill the subpopulation of malignant cells with vigorous proliferation or a certain target, which is a lack of integrity. Because of the heterogeneity of tumor cells and tumor cells have a high frequency of genetic variation across space in time, no matter which Modern medicine will eventually lead to drug resistance, which become an unresolvable bottleneck. Consequently, traditional Chinese medicine are natural products, which is an important supplement to breast cancer treatment with synergistic and attenuated effects, especially the treatment can reduce the perioperative complications, the toxicity and side effects during chemotherapy, and help to improve the quality of life of patients during treatment. At this stage, the traditional Chinese medicinal prescriptions which obtained small samples of clinical evidence-based medicine to prove the effectiveness, and used in clinical practice are: Sanyin Formula after Breast Cancer Surgery, Louci Sanjie Recipe, Huaier Granules, Compound Tubeimu (Bolbostemmatis Rhizoma) Preparation, Compound Banmao Capsules, Compound Hong-dou-shan Formula, there are also some problems in the above Chinese medicine prescriptions: firstly, the treatment effect is not significant based on the independent application of traditional Chinese medicine prescriptions, the treatment effect can be increased by combining with Modern medicine, but the time and frequency of Modern medicine cannot be reduced; secondly, most of the prescriptions used in clinical practice come from classical famous prescriptions, that is, prescriptions recorded in ancient books of traditional Chinese medicine, which are added or subtracted according to syndrome differentiation, and innovative prescriptions are rare.

SUMMARY

A primary objective of the present invention is to solve the problems of side effects and drug resistance of present prescription for treating breast cancer diseases during the treatment process;

- another objective of the present invention is to solve the current problem that the traditional Chinese medicines used in the treatment of breast cancer diseases come from the prescriptions recorded in the ancient books of traditional Chinese medicines, resulting in uncertain efficacy and rare innovative prescriptions;
- additionally, another objective of the present invention is to solve the problem that the traditional Chinese medicine used in the treatment of breast cancer diseases is currently used in combination with Modern medicine, which cannot reduce the dose and frequency of application of Modern medicine.

In order to achieve the above objectives and solve the above problems, a drug for a treatment of breast cancer with antler and ginseng as a sovereign drug and preparation method and application thereof is provided.

The drug for treating breast cancer provided by the present invention is made of antler and ginseng as the sovereign drug, *Angelicae sinensis radix* and *Radix paeoniae alba* as the adjuvant drug, and combined with *Radix bupleuri, Scutellariae radix, Cyperi rhizoma* and thunberg fritillary bulb; wherein the contents of each ingredient in the above-mentioned: 12 parts of antler, 3 parts of ginseng, 10 parts of *Angelicae sinensis radix,* 10 parts of *Radix paeoniae alba,* 5 parts of *Radix bupleuri,* 5 parts of *Scutellariae radix,* 10 parts of *Cyperi rhizoma* and 10 parts of thunberg fritillary bulb.

The present invention provides a preparation method for a drug for treatment of breast cancer with antler and ginseng as sovereign drugs, including the following steps:

- step 1, taking 12 parts of antler and 3 parts of ginseng by weight and soaking separately;
- step 2, taking 10 parts of *Angelicae sinensis radix,* 10 parts of *Radix paeoniae alba,* 5 parts of *Radix bupleuri,* 5 parts of *Scutellariae radix,* 10 parts of *Cyperi rhizoma* and 10 parts of thunberg fritillary bulb by weight and adding water of 8 times a total weight of the above-mentioned ingredients to fully immerse;
- step 3, decocting 12 parts of the antler soaked in step 1 for 0.5 h, then adding 10 parts of *Angelicae sinensis radix,* 10 parts of *Radix paeoniae alba,* 5 parts of *Radix bupleuri,* 5 parts of *Scutellariae radix,* 10 parts of *Cyperi rhizoma* and 10 parts of thunberg fritillary bulb soaked in step 2 and continuing to decoct the solution;
- step 4, separately decocting 3 parts of the ginseng soaked in step 1, and adding a decocted ginseng aqueous solution into the decocted pharmaceutical decoction in step 3; completing the decocting for 3 times, 2 h each time, filtering by gauze and combining filtrate for 3 times; and
- step 5, compressing the filtrate obtained in step 4 to a paste by a rotary evaporator under reduced pressure, and placing the extract in a freeze dryer, pre-freezing at −20° C. for 12 h, sublimation-drying at room temperature for 24 h, and then placing in a vacuum dryer for 48 h, after completion of drying, turning off a vacuum pump, and collecting a dry powder sample, and sealing and storing the sample at −20° C. for future use.

The present invention provides an application of a drug prepared with antler and ginseng as a sovereign drug (hereinafter referred to as Antler-Ginseng compound preparation) in the treatment of breast cancer.

The mechanism of action of each ingredient of the above-mentioned drug is as follows:

the antlers can restore the disordered sex hormone axis to normal. The disorder of sex hormones is an important cause of breast cancer. On this basis, the cell experiments and animal experiments showed that antler base could inhibit the invasion, epithelial-mesenchymal transition (EMT), cancer stem cells and metastasis of breast cancer, and had a certain preventive effect on the formation of hormone receptor positive breast cancer. Mechanistic studies have shown that the antler base exerts anti-tumor effects through the extracellular matrix TENASCIN and NF-κB.

Ginseng also has a certain effect on tumor patients: ginseng is a traditional Chinese medicine with a long history, the ginsenosides as an active ingredient of ginseng can inhibit the rapid proliferation of tumor cells to a certain extent, promote tumor cell apoptosis, restore the sensitivity of chemotherapeutic drugs on tumor cells, and inhibit tumor metastasis and invasion, additionally, the ginsenosides combines with chemotherapeutic drugs can increase its efficacy and reduce side effects. A variety of ginseng extracts have a significant inhibitory effect on MCF-7 cell proliferation and EMT by blocking certain signal transduction pathways in cells, such as ginsenoside CK; ginsenoside Rh1 is a protopanaxatriol-type ginsenoside extract, which can inhibit ROS-mediated PI3K/AKT (serine/threonine kinase) signaling pathway, arrest tumor cell cycle in the early stage of cells, promote cell apoptosis, and has certain anti-tumor activity; ginsenoside Rh4 can induce apoptosis by reducing Bcl-2, increasing Bax, and activating Caspase-9, Caspase-3 and PARP (Poly-ADP-Ribose-Polymerase), ginseng can change the sensitivity to chemotherapeutic drugs, promote cancer cell apoptosis, thereby controlling the progress of breast cancer.

*Radix bupleuri* and *Scutellariae radix* are used as adjuvant drugs to regulate the unsmooth situation of Shaoyang Pivot (Shaoyang meridian is one of the six meridians of the human body, which is mainly responsible for regulating the operation of qi and blood and emotional changes in the human body. When Shaoyang pivot is unfavorable, the body's qi and blood circulation will be affected, and symptoms such as stagnation of qi and blood stasis and body fluid coagulation will occur), Shaoyang belongs to the meridian of half-exterior and half-interior in the human body, it is mainly responsible for the opening and closing of the pivot, which can make the Qi of Yin and Yang smoothly accessible (Qi is also called the Vital Force, qi refers both to the refined nutritive substance that flows within the human body as well as to its functional activities, the balance of qi in the parts of the body depends on the flow of various kinds of qi and fluids, where injury, physical suffering, and lack of proper food causes a qi deficiency; Yin and Yang are the summarization of attributes of two opposite aspects of interrelated things or phenomena in nature, and to explain the phenomena and essences of the whole universe and life. Where Yin is static, dark, cold, substantial, dimness, and stillness; Yang is dynamic, bright, hot, functional brightness, and movement). The Qi Activity of the human body from the surface to the inside, from the inside to the outside, as well as the upper and lower organs have to rely on Shaoyang Qi Activity to play a pivotal role. The Shaoyang meridian disease cannot adopt sweat, lower temperature, or interior-warming methods, only with the method of reconciliation. The combination of the three herbs of *Radix bupleuri, Scutellariae radix* and ginseng mentioned above is a reference to the meaning of xiaochaihu decoction to reconcile Shaoyang. *Radix bupleuri* is pungent, and disperses stagnated liver Qi for relieving Qi stagnation, and increasing Yang Qi of Shaoyang; Shaoyang gallbladder is a wood in Wuxing (the Five Elements, wherein the five elements refer to wood, fire, earth, metal and water as well as their motion and changes in natural world, also known as five phases), the Qi of dampness and heat is particularly easy to be depressed in the gallbladder, the taste of *Scutellariae radix* is acrid and cold, it can clear heat and dry dampness, and is good for removing the dampness and heat in the gallbladder. Ginseng can tonify the middle warmer, and strengthen Vital Qi (Vital Qi is a collective designation for all normal functions of the human body and the abilities to maintain health, including the abilities of self-regulation, adaptation, also known as healthy qi), so as to prevent injury to the middle warmer. Shaoyang exterior-interior Qi Activity runs normally, the damp heat will be cleaned up, and then together with *Radix bupleuri* to form a prescription similar to Xiaoyaosan, it can play the role of dispersing stagnated liver Qi for relieving Qi stagnation, nourishing blood and strengthening spleen. *Angelicae sinensis radix* tastes sweet, pungent, acrid, and mild, it can not only nourish the blood and can reconcile the blood, but also it tastes pungent and can diverge, which is Qi-tonifying medicinal for blood. The *Radix paeoniae alba* tastes sour and acrid, slightly cold, it can nourish the blood and converge the Yang Qi, soften the liver, and relieve some urgent symptoms; *Radix angelicae sinensis* and *Radix paeoniae alba* are used together with *Radix bupleuri* for tonifying the liver and assisting the liver, so that the blood is harmonized and the liver is harmonized, and blood is sufficient, the liver is healthy, the above-mentioned drugs are all adjuvant drug. *Cyperi rhizoma* is pungent and can enter the liver meridian, it is a good medicine commonly used in gynecology, it is especially good at soothing the liver, promoting Qi and relieving pain; thunberg fritillary bulb is used for harmonizing and releasing stored coldness and dampness to facilitate the dispersion of congealed masses in the body. In clinical practice, thunberg fritillary bulb is often used to treat scrofula, goiter, sore carbuncle, lung carbuncle, etc. The combination of *Cyperi rhizoma* and thunberg fritillary bulb can use acrid purging to relieve heat and detoxification, expel stagnation and eliminate stagnation, and be used to treat diseases such as scrofula and phlegm. Among these drugs, the sovereign drug antler is a flesh and blood medicinal product, which can tonify the innate essence, and then be matched with ginseng, which can greatly tonify the vitality and make the spleen and stomach healthier, so as to help acquire vital genesis of Qi and blood biochemistry. In addition, it also cooperates with *Radix bupleuri, Scutellariae radix, Angelicae sinensis radix, Radix paeoniae alba* and other drugs to evacuate the unsmooth situation of Shaoyang Pivot, it can also soften the liver, nourish Qi and blood, and then play the role of removing blood stasis and resolving masses with other drugs.

The beneficial effects of the present invention are as follows:

According to the present invention, the drug using antler and ginseng as the sovereign drug for the treatment of breast cancer can be clinically used in the prescription for the treatment of breast cancer, and some clinical cases were observed, including 30 women with high-risk breast cancer factors and 11 patients with breast cancer receiving neoadjuvant therapy and rescue therapy, all of whom achieved good efficacy in combination with Modern medicine. During the period that some patients had drug resistance or side effects of Modern medicine to stop that Modern medicine treatment, the Antler-Ginseng compound preparation effectively controlled the development of tumors, and all patients had no adverse reactions. Antler has the effects of nourishing the liver and tonifying the kidney, strengthening muscles and bones, and promoting blood circulation to remove edema. Therefore, it can be determined that using antlers as a sovereign drug to constitute a prescription for treating breast cancer is effective. Ginsenosides in the medicine of the present invention can significantly modulate the immune regulation function in the human body, change the direct resistance of tumor cells to certain chemical drugs in the body, alleviate the chronic liver and kidney toxicity caused by certain chemotherapeutic drugs, protect the central nervous system of the human body, regulate the system function, resist fatigue and repair the wound, etc. Finally, animal experiments were carried out again and the clinical observation confirmed that the types and frequency of Modern medicine can be reduced, the progression of primary breast cancer lesions is significantly reduced and the efficacy of metastasis also reduced. During the chemotherapy period, it can also effectively reduce chemotherapy toxicity, side effects and inhibit metastasis.

The present invention provides that the main active ingredients of Antler-Ginseng compound preparation for treating breast cancer represented by triple-negative can tightly bind to the corresponding target protein and have good binding energy, thereby exerting a pharmacodynamic effect. In addition, molecular docking results showed that the docking targets are closely related to cancer pathways, such as TP53, AKT1, SRC, IL6, ESR1 and so on, mainly involved in oncogenes, tumor suppressor genes, signal transduction, tumor immunity, chromosome mutation and other issues, further proved that the active ingredients of Antler-Ginseng compound preparation could interfere the occurrence and development of breast cancer by acting on cancer-related targets and related signaling pathways.

Typical clinical cases are as follows:

Typical clinical case 1: patients suffered from advanced breast cancer with liver metastasis were treated with the targeted drug Abemaciclib and the endocrine drug Fulvestrant for 3 days, the liver function showed that the transaminase increased by 10 times, then the targeted drug Abemaciclib was discontinued and the Antler-Ginseng compound preparation provided by the present invention was used for treatment, after 2 months, the liver metastasis was evaluated to be stable and did not progress, and the liver function returned to normal.

Typical clinical case 2: patients suffered from breast cancer with bone metastasis were treated with endocrine therapy and CDK4/6 targeted therapy, during the treatment, the breast lesions progressed twice, the third-line treatment was treated with TX regimen chemotherapy, and the lesions progressed again after the third cycle, then the Antler-Ginseng compound preparation provided by the present invention was used for three weeks, and Color Doppler ultrasound showed that the lesions had apparent shrinkage, which size is from 29.2×20 mm to 27.9×18.1 mm.

Typical clinical case 3: patients with bone and liver metastasis of advanced breast cancer, the first line was treated with the fourth cycle of TX chemotherapy, the breast target lesion progressed, then the Antler-Ginseng compound preparation provided by the present invention was used for treatment, and Color Doppler ultrasound showed that the breast target lesion had apparent shrinkage, which from 53.9×17.6 mm to 43.3×17.4 mm.

BRIEF DESCRIPTION OF THE DRAWINGS

FIGS. 3A-3B are schematic diagrams of a mouse tumor growth curve and tumor volume according to the present invention, wherein: FIG. 3A is a tumor growth curve of mice in each group, FIG. 3B is a mean volume of in vivo tumors of mice in each group, *$P<0.05$  $P<0.01$ ** $P<0.00$.

FIGS. 4A-4B are schematic diagrams of a weight and a tumor inhibition rate of mice in each group according to the present invention, wherein: FIG. 4A is a tumor weight of mice in each group, FIG. 4B is a tumor inhibition rate of each treatment group, *$P<0.05$  $P<0.01$ ** $P<0.001$.

FIGS. 8A-8D are bubble schematic diagrams of the functional enrichment of Gene Ontology (GO) as a potential target for the treatment of triple-negative breast cancer by the Antler-Ginseng compound preparation in the present invention, wherein: FIG. 8A: biological process (BP), FIG. 8B: cell composition (CC), FIG. 8C: molecular function (MF).

FIGS. 9A-9B are schematic diagrams of Kyoto Encyclopedia of Genes and Genomes (KEGG) enrichment of a potential target for the treatment of breast cancer with the Antler-Ginseng compound preparation of the present invention; wherein: FIG. 9A: top 20 enrichment pathways, FIG. 9B: KEGG top 20 enrichment bubble diagram.

DETAILED DESCRIPTION OF THE EMBODIMENTS

Figures 1, 2:
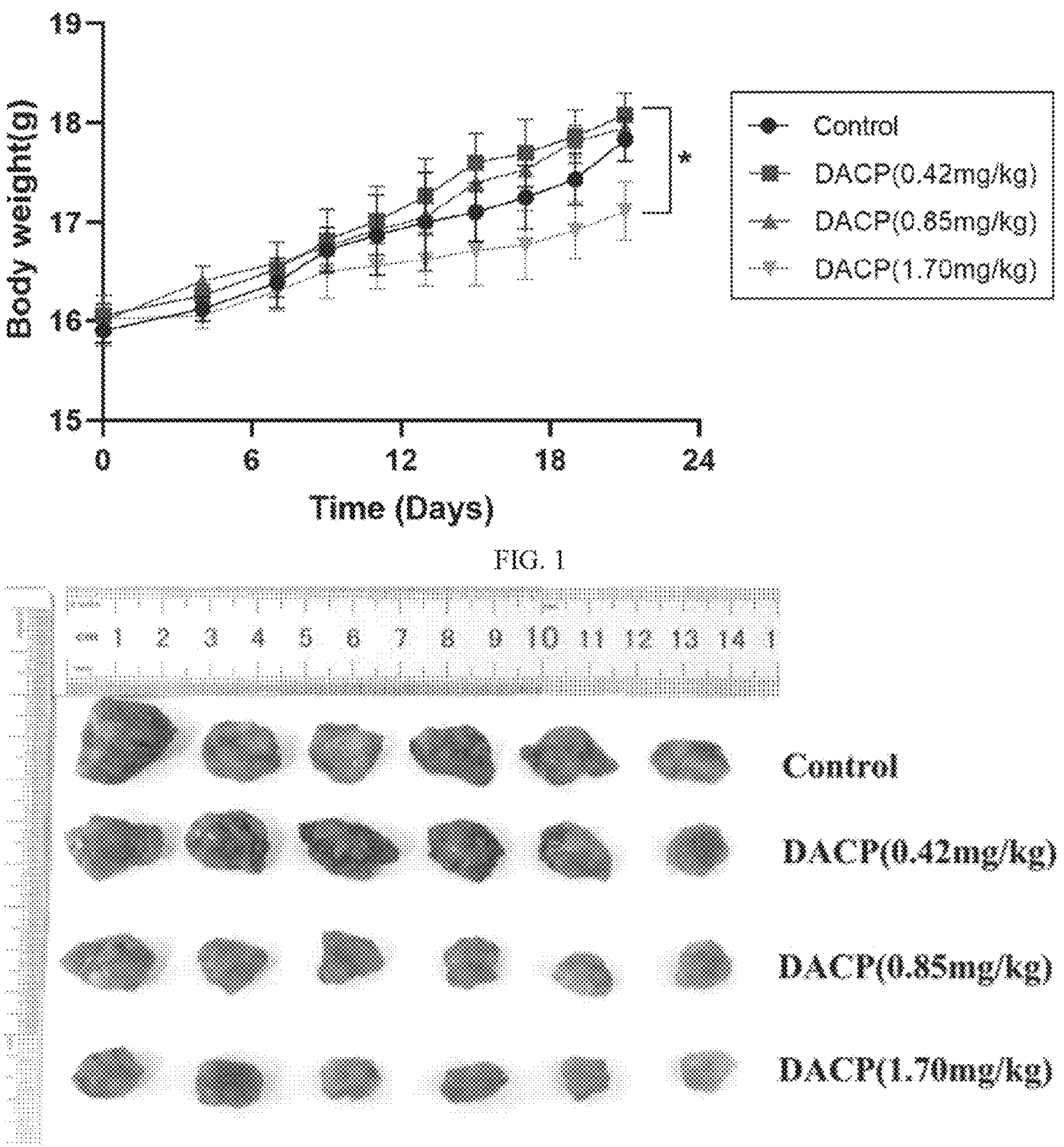
FIG. 1 is a schematic diagram of a body weight of each group of mice in the experiments according to the present invention with the group of different dose comparing to the group of normal saline.
FIG. 2 is a schematic diagram of an appearance of an in vitro tumor from each group of mice according to the present invention.

With reference to FIGS. 1-13:

The drug for treating breast cancer with antler and ginseng provided by the present invention is made of antler and ginseng as the sovereign drug, *Angelicae sinensis radix* and *Radix paeoniae alba* as the adjuvant drug, and combined with *Radix bupleuri, Scutellariae radix, Cyperi rhizoma* and thunberg fritillary bulb; wherein the contents of each ingredient in the above-mentioned: 12 parts of antler, 3 parts of ginseng, 10 parts of *Angelicae sinensis radix,* 10 parts of *Radix paeoniae alba,* 5 parts of *Radix bupleuri,* 5 parts of *Scutellariae radix,* 10 parts of *Cyperi rhizoma* and 10 parts of thunberg fritillary bulb.

The present invention provides a preparation method for a drug for treatment of breast cancer with antler and ginseng as a sovereign drug, including the following steps:

step 1, 12 parts of antler and 3 parts of ginseng are taken by weight and soaked separately;

step 2, 10 parts of *Angelicae sinensis radix,* 10 parts of *Radix paeoniae alba,* 5 parts of *Radix bupleuri,* 5 parts of *Scutellariae radix,* 10 parts of *Cyperi rhizoma* and 10 parts of thunberg fritillary bulb are taken by weight and water of 8 times a total weight of the above-mentioned ingredients is added to fully immerse;

step 3, 12 parts of the antler soaked in step 1 are decocted for 0.5 h, then 10 parts of *Angelicae sinensis radix,* 10 parts of *Radix paeoniae alba,* 5 parts of *Radix bupleuri,* 5 parts of *Scutellariae radix,* 10 parts of *Cyperi rhizoma* and 10 parts of thunberg fritillary bulb soaked in step 2 are added and continued to decoct the solution;

step 4, 3 parts of the ginseng soaked in step 1 are separately decocted, and a decocted ginseng aqueous solution is added into the decocted pharmaceutical decoction in step 3; the decocting is completed for 3 times, 2 h each time, gauze filtered and combined filtrate for 3 times; and step 5, the filtrate obtained in step 4 is compressed to a paste by a rotary evaporator under reduced pressure, and the extract is placed in a freeze dryer, pre-freezed at −20° C. for 12 h, sublimation-dried at room temperature for 24 h, and then placed in a vacuum dryer for 48 h, after completion of drying, a vacuum pump is turned off, and a dry powder sample is collected, and the sample is sealed and stored at −20° C. for future use.

The present invention provides an application of a drug prepared with antler and ginseng as a sovereign drug (hereinafter referred to as Antler-Ginseng compound preparation) in the treatment of breast cancer.

The mechanism of action of each ingredient of the above-mentioned drug is as follows:

the antlers can restore the disordered sex hormone axis to normal. The disorder of sex hormones is an important cause of breast cancer. On this basis, the cell experiments and animal experiments showed that antler base could inhibit the invasion, epithelial-mesenchymal transition (EMT), cancer stem cells and metastasis of breast cancer, and had a certain preventive effect on the formation of hormone receptor positive breast cancer. Mechanistic studies have shown that the antler base exerts anti-tumor effects through the extracellular matrix TENASCIN and NF-κB.

Ginseng also has a certain effect on tumor patients: ginseng is a traditional Chinese medicine with a long history, the ginsenosides as an active ingredient of ginseng can inhibit the rapid proliferation of tumor cells to a certain extent, promote tumor cell apoptosis, restore the sensitivity of chemotherapeutic drugs on tumor cells, and inhibit tumor metastasis and invasion, additionally, combined use with chemotherapeutic drugs can increase its efficacy and reduce side effects. A variety of ginseng extracts have a significant inhibitory effect on MCF-7 cell proliferation and epithelial-mesenchymal transition (EMT) by blocking certain signal transduction pathways in cells, such as ginsenoside CK. Ginsenoside Rh1 is a protopanaxatriol-type ginsenoside extract, which can inhibit ROS-mediated PI3K/AKT signaling pathway, promote tumor cell cycle arrest in the early stage of cells, promote cell apoptosis, and has certain anti-tumor activity. Ginsenoside Rh4 can induce apoptosis by reducing Bcl-2, increasing Bax, and activating Caspase-9, Caspase-3 and PARP, ginseng can change the sensitivity to chemotherapeutic drugs, promote cancer cell apoptosis, thereby controlling the progress of breast cancer.

*Radix bupleuri* and *Scutellariae radix* are used as adjuvant drugs to regulate the unsmooth situation of Shaoyang Pivot (Shaoyang meridian is one of the six meridians of the human body, which is mainly responsible for regulating the operation of qi and blood and emotional changes in the human body. When Shaoyang pivot is unfavorable, the body's qi and blood circulation will be affected, and symptoms such as stagnation of qi and blood stasis and body fluid coagulation will occur.), Shaoyang belongs to the meridian of half-exterior and half-interior in the human body, it is mainly responsible for the opening and closing of the pivot, which can make the Qi of Yin and Yang smoothly accessible (wherein Qi is also called the Vital Force, qi refers both to the refined nutritive substance that flows within the human body as well as to its functional activities, the balance of qi in the parts of the body depends on the flow of various kinds of qi and fluids, where injury, physical suffering, and lack of proper food causes a qi deficiency; Yin and Yang are the summarization of attributes of two opposite aspects of interrelated things or phenomena in nature, and to explain the phenomena and essences of the whole universe and life. Where Yin is static, dark, cold, substantial, dimness, and stillness; Yang is dynamic, bright, hot, functional brightness, and movement). The Qi Activity of the human body from the surface to the inside, from the inside to the outside, as well as the upper and lower organs have to rely on Shaoyang Qi Activity to play a pivotal role. The Shaoyang meridian disease cannot adopt sweat, lower temperature, or interior-warming methods, only with the method of reconciliation. The combination of the three herbs of *Radix bupleuri, Scutellariae radix* and ginseng mentioned above is a reference to the meaning of xiaochaihu decoction to reconcile Shaoyang. *Radix bupleuri* is pungent, and disperses stagnated liver Qi for relieving Qi stagnation, and increasing Yang Qi of Shaoyang; Shaoyang gallbladder is a wood in Wuxing (the Five Elements, wherein the five elements refer to wood, fire, earth, metal and water as well as their motion and changes in natural world, also known as five phases), the Qi of dampness and heat is particularly easy to be depressed in the gallbladder, the taste of *Scutellariae radix* is acrid and cold, it can clear heat and dry dampness, and is good for removing the dampness and heat in the gallbladder. Ginseng can tonify the middle warmer, and strengthen Vital Qi (Vital Qi is a collective designation for all normal functions of the human body and the abilities to maintain health, including the abilities of self-regulation, adaptation, also known as healthy qi), so as to prevent injury to the middle warmer. Shaoyang exterior-interior Qi Activity runs normally, the damp heat will be cleaned up, and then together with *Radix bupleuri* to form a prescription similar to Xiaoyaosan, it can play the role of dispersing stagnated liver Qi for relieving Qi stagnation, nourishing blood and strengthening spleen. *Angelicae sinensis radix* tastes sweet, pungent, acrid, and mild, it can not only nourish the blood and can reconcile the blood, but also it tastes pungent and can diverge, which is Qi-tonifying medicinal for blood. The *Radix paeoniae alba* tastes sour and acrid, slightly cold, it can nourish the blood and converge the Yang Qi, soften the liver, and relieve some urgent symptoms; *Radix angelicae sinensis* and *Radix paeoniae alba* are used together with *Radix bupleuri* for tonifying the liver and assisting the liver, so that the blood is harmonized and the liver is harmonized, and blood is sufficient, the liver is healthy, the above-mentioned drugs are all adjuvant drug. *Cyperi rhizoma* is pungent and can enter the liver meridian, it is a good medicine commonly used in gynecology, it is especially good at soothing the liver, promoting Qi and relieving pain; thunberg fritillary bulb is used for harmonizing and releasing stored coldness and dampness to facilitate the dispersion of congealed masses in the body. In clinical practice, thunberg fritillary bulb is often used to treat scrofula, goiter, sore carbuncle, lung carbuncle, etc. The combination of *Cyperi rhizoma* and thunberg fritillary bulb can use acrid purging to relieve heat and detoxification, expel stagnation and eliminate stagnation, and be used to treat diseases such as scrofula and phlegm. Among these drugs, the sovereign drug antler is a flesh and blood medicinal product, which can tonify the innate essence, and then be matched with ginseng, which can greatly tonify the vitality and make the spleen and stomach healthier, so as to help acquire vital genesis of Qi and blood biochemistry. In addition, it also cooperates with *Radix bupleuri, Scutellariae radix, Angelicae sinensis radix, Radix paeoniae alba* and other drugs to evacuate the unsmooth situation of Shaoyang Pivot, it can also soften the liver, nourish Qi and blood, and then play the role of removing blood stasis and resolving masses with other drugs.

The specific experiments for the above-mentioned drug are as follows:

1. Setting for Drug Dose:

according to the corresponding pharmacopoeia, the adult dose of the Antler-Ginseng compound preparation provided by the present invention is 65 g/d, and the conversion coefficient between mice and humans is 0.0026 based on the average weight of a human is 60 kg. The clinical equivalent dose of Antler-Ginseng compound preparation for mice is 8.45 g/kg/d, and the dose obtained by the above method is a middle dose, therefore, the low dose is half of middle dose 4.23 g/kg/d, and the high dose is double middle dose 16.90 g/kg/d.

2. Establishment of 4T1 Triple-Negative Mice Breast Cancer Model:

after the required amount of 4T1 breast cancer cells were cultured, the cells were resuspended in phosphate-buffered saline (PBS) after trypsin digestion and centrifugation, and the cells were counted and diluted to a cell concentration of $1\times10^7$ cells/mL. All mice were intraperitoneally injected with 50 mg/kg pentobarbital sodium and 0.5% lidocaine solution for infiltration anesthesia, under anesthesia, 0.1 mL cell suspension of each mouse was inoculated in the third pair of mammary fat pads on the left side, the cotton swab was pressed for a moment to avoid cell outflow after inoculation. During the inoculation process, the pipette blows the cell suspension to ensure uniform suspension.

3. Grouping for the First Batch of Animal Experiment Groups:

BALB/c mice were randomly divided into 4 groups, which were divided into PBS control group, 0.42 mg/mL low dose group of Antler-Ginseng compound preparation (DACP-L), 0.85 mg/mL medium dose group of Antler-Ginseng compound preparation (DACP-M) and 1.70 mg/mL high dose group of Antler-Ginseng compound preparation (DACP-H), with 6 mice in each group. On the second day after tumor implantation, the mice were administered by gavage with different doses of 0.2 mL/mouse, and continuous administration for 21 days.

4. Grouping for the Second Batch of Animal Experiment Groups:

experimental BALB/c mice were divided into 3 groups with 10 mice in each group. They were the PBS group, chemotherapy paclitaxel (DTX) group, and DTX+medium dose (0.85 mg/kg) group.

The mice were administered by gavage on the second day after tumor implantation, the DTX group was intraperitoneally injected with 0.2 mL of DTX, once a week. The DTX+medium dose group was intraperitoneally injected with DTX at the first and fourth weeks of inoculation and combined with the medium dose of Antler-Ginseng compound preparation. The tumor volume ($L\times W2\times0.4$) and body weight of mice were measured on the 7th day after inoculation. For a total of 31 days. Flow cytometry analysis: three mice in each group of PBS group and DTX+medium dose group were selected randomly for flow cytometry analysis of tumor tissue and spleen. All statistical analyses were performed by using GraphPad Prism 9.0, $P<0.05$ was considered statistically significant.

The experimental results are as follows:

1. Weight Changes of Mice in Each Group of First Batch:

The changes of the body weight of mice in each group before and after administration are shown in FIG. 1, there was no significant difference in the body weight of mice in each group before administration, the body weight of each group gradually increased after administration, the growth rate of DACP-L was faster, while the growth rate of DACP-H was slower, after 21 days of administration, there was no significant difference in body weight among the control group, low concentration group and medium concentration group.

2. The Appearance of Tumors In Vitro of Mice in Each Group:

the tumor-bearing mice were administered by gavage for 21 days, and the mice were euthanized after anesthesia. The appearance of the tumor tissue was photographed to preserve after blunt dissection, as shown in FIG. 2, and the tumor tissue was observed by eyes and measured, the tumor size of the control group was significantly larger than the tumor size of the medium and high concentration of the drug, and the tumor size of the drug group gradually decreased with the increase of the drug dose.

Figures 3A, 3B:
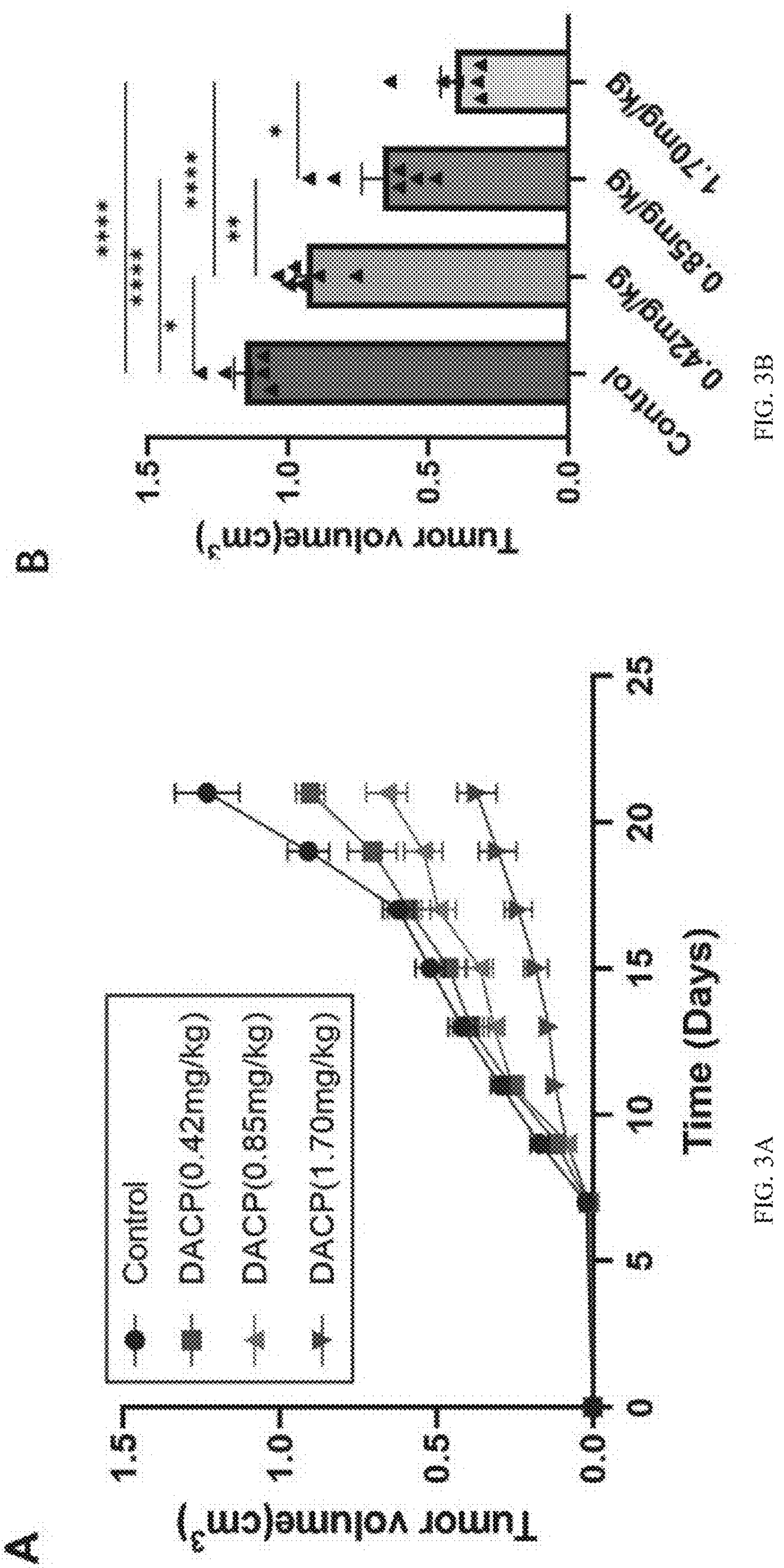

3. Tumor Growth Curve and Tumor Volume of Mice in Each Group:

the tumor growth curve of each group of mice is shown in FIG. 3A, from the 7th day of tumor inoculation, the tumor volume of each group showed a growing trend, wherein there was no significant difference in the growth rate between the Con group and the DACP-L group on the first 17 days, from the 17th day, the tumor growth of the Con group increased significantly, the tumor growth rate of the DACP group was slower at the manner of dose dependent than the growth rate of the Con group.

The tumor volume of the mice after euthanasia was bluntly separated as shown in FIG. 3B, where the tumor volume of each drug treatment group was significantly smaller than the tumor volume of the Con group ($P<0.05$). Compared the tumor volume of the drug treatment group with the control group, the tumor volume of the DACP-L group was significantly smaller than the tumor volume of the Con group ($P<0.05$), and the tumor volume of the DACP-M group and the DACP-H group was significantly smaller than the tumor volume of the Con group ($P<0.001$). Compared the tumor volume between treatment groups, the tumor volume of DACP-H group was significantly smaller than the tumor volume of DACP-M group ($P<0.01$), the tumor volume of DACP-H group was very significantly smaller than the tumor volume of DACP-L group (P<0.001), the tumor volume of DACP-M group was significantly smaller than the tumor volume of DACP-L group (P<0.05).

Figures 4A, 4B:
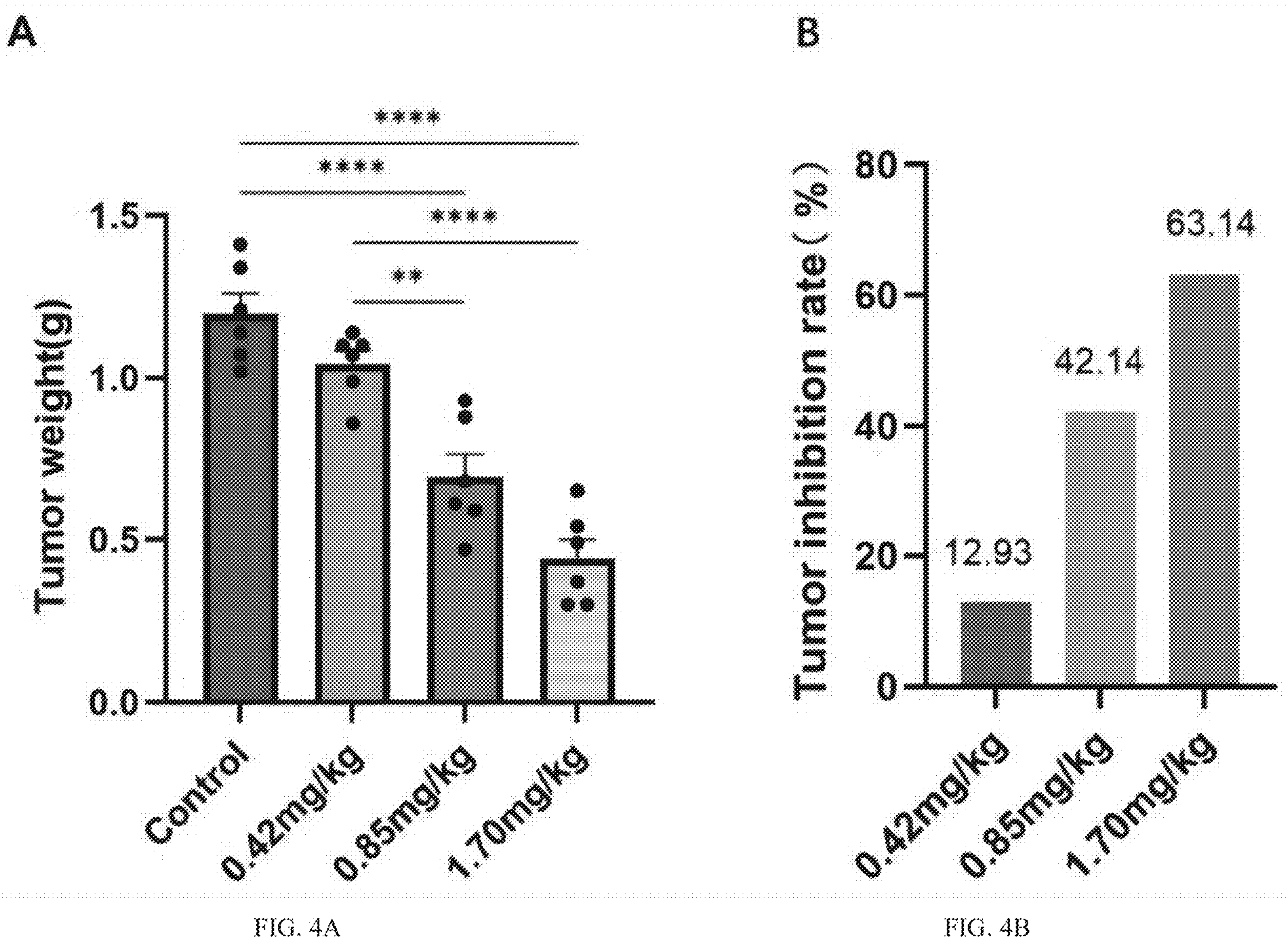

4. Tumor Weight and Tumor Inhibition Rate of Mice in Each Group:

the tumor weight of mice in each group is shown in Table 1 and FIG. 4A, different doses of Antler-Ginseng compound preparation gavage treatment effectively reduced the tumor weight, the final tumor weight of mice in the Con group was 1.2±0.15 g while that was 1.04±0.10 g in the DACP-L group, 0.69±0.18 g in the DACP-M group and 0.44±0.14 g in the DACP-L group. Compared with the Con group, the tumor weight of the DACP-L group in the drug treatment group decreased, but the difference was not significant (P>0.05), and the tumor weight of the DACP-M group and the DACP-H group decreased significantly (P<0.001). Meanwhile, tumor weight between treatment groups were inhibited at the manner of dose dependence. The tumor weight of the DACP-M group and DACP-H group was significantly lower than the tumor weight of the DACP-L group (P<0.001), the tumor weight of DACP-H group was lower than the tumor weight of DACP-M group, but the difference was not significant (P>0.05).

The tumor inhibition rate of each treatment group is shown in Table 1 and FIG. 4B. Different concentrations of Antler-Ginseng compound preparation can inhibit tumor growth through administered by gavage, with the increase of drug dose, the tumor inhibition rates of DACP-L, DACP-M and DACP-H groups increased gradually, which were 12.93%, 42.14% and 63.14%, respectively. The DACP-H group had a significant tumor inhibition rate of more than 50%.

TABLE 1

Effect of Antler-Ginseng compound preparation on tumor growth in mice (x ± s, n = 6)

| Group | Dose (mg/kg) | Tumor weight (g) | Tumor inhibition rate (%) | Body weight (g) | Spleen index (%) |
|---|---|---|---|---|---|
| Control | — | 1.2 ± 0.15 | — | 17.83 ± 0.54 | 1.33 ± 11.52 |
| DACP-L | 0.42 | 1.04 ± 0.10 | 12.93 | 18.08 ± 0.54 | 35.26 ± 5.57 |
| DACP-M | 0.85 | 0.69 ± 0.18 | 42.14 | 17.95 ± 0.23 | 33.25 ± 5.61 |
| DACP-H | 1.70 | 0.44 ± 0.14 | 63.14 | 17.12 ± 0.72 | 30.31 ± 9.99 |

To confirm the quality of Antler-Ginseng compound preparation, its composition was analyzed using HPLC (Liquid Chromatograph Mass Spectrometer/Mass Spectrometer). A total of 388 compounds in Antler-Ginseng compound preparation, were examined by LC-MS/MS and analyzed through Network pharmacology (Table. 2A and 2B). Among the compounds identified were 68 flavonoids, 48 pregnenolone lipids, 40 carboxylic acids, and their derivatives, and 40 benzene and its substituted derivatives. Additionally, there were 32 other compounds, 29 organic oxygen compounds, and 23 fatty acyls. The remaining compounds included furans, coumarins and their derivatives, isoflavones, and various other substances.

TABLE 2A

The MW, ID, OB, and DL of active compounds in Antler-Ginseng compound preparation

| MOLID | Active Ingredients | MW | OB | DL | TCM |
|---|---|---|---|---|---|
| MOL001918 | paeoniflorgenone | 318.35 | 87.59 | 0.37 | BS1 |
| MOL001919 | Palbinone | 358.52 | 43.56 | 0.53 | BS2 |
| MOL001924 | paeoniflorin | 480.51 | 53.87 | 0.79 | BS3 |
| MOL000211 | Mairin | 456.78 | 55.38 | 0.78 | BS4 |
| MOL000492 | (+)-catechin | 290.29 | 54.83 | 0.24 | BS5 |
| MOL000490 | petunidin | 317.29 | 30.05 | 0.31 | CH1 |
| MOL001645 | Linoleyl acetate | 308.56 | 42.1 | 0.2 | CH2 |
| MOL002776 | Baicalin | 446.39 | 40.12 | 0.75 | CH3 |
| MOL004598 | 3',4',5',3,5,6,7-Heptamethoxyflavone | 432.46 | 31.97 | 0.59 | CH4 |
| MOL004609 | Areapillin | 360.34 | 48.96 | 0.41 | CH5 |
| MOL004624 | Longikaurin A | 348.48 | 47.72 | 0.53 | CH6 |
| MOL004653 | (+)-Anomalin | 426.5 | 46.06 | 0.66 | CH7 |
| MOL004718 | α-spinasterol | 412.77 | 42.98 | 0.76 | CH8 |
| MOL013187 | Cubebin | 356.4 | 57.13 | 0.64 | CH9 |
| MOL000073 | ent-Epicatechin | 290.29 | 48.96 | 0.24 | HQ1 |
| MOL000173 | wogonin | 284.28 | 30.68 | 0.23 | HQ2 |
| MOL000228 | (2R)-7-hydroxy-5-methoxy-2-phenylchroman-4-one | 270.3 | 55.23 | 0.2 | HQ3 |
| MOL000525 | Norwogonin | 270.25 | 39.4 | 0.21 | HQ4 |
| MOL000552 | 5,2'-Dihydroxy-6,7,8-trimethoxyflavone | 344.34 | 31.71 | 0.35 | HQ5 |

TABLE 2A-continued

The MW, ID, OB, and DL of active compounds in Antler-Ginseng compound preparation

| MOLID | Active Ingredients | MW | OB | DL | TCM |
|---|---|---|---|---|---|
| MOL001458 | coptisine | 320.34 | 30.67 | 0.86 | HQ6 |
| MOL001490 | bis[(2S)-2-ethylhexyl] benzene-1,2-dicarboxylate | 390.62 | 43.59 | 0.35 | HQ7 |
| MOL001689 | acacetin | 284.28 | 34.97 | 0.24 | HQ8 |
| MOL002714 | baicalein | 270.25 | 33.52 | 0.21 | HQ9 |
| MOL002897 | epiberberine | 336.39 | 43.09 | 0.78 | HQ10 |
| MOL002909 | 5,7,2,5-tetrahydroxy-8,6-dimethoxyflavone | 376.34 | 33.82 | 0.45 | HQ11 |
| MOL002910 | Carthamidin | 288.27 | 41.15 | 0.24 | HQ12 |
| MOL002913 | Dihydrobaicalin_qt | 272.27 | 40.04 | 0.21 | HQ13 |
| MOL002914 | Eriodyctiol (flavanone) | 288.27 | 41.35 | 0.24 | HQ14 |
| MOL002915 | Salvigenin | 328.34 | 49.07 | 0.33 | HQ15 |
| MOL002917 | 5,2',6'-Trihydroxy-7,8-dimethoxyflavone | 330.31 | 45.05 | 0.33 | HQ16 |
| MOL002925 | 5,7,2',6'-Tetrahydroxyflavone | 286.25 | 37.01 | 0.24 | HQ17 |
| MOL002927 | Skullcapflavone II | 374.37 | 69.51 | 0.44 | HQ18 |
| MOL002928 | oroxylin a | 284.28 | 41.37 | 0.23 | HQ19 |
| MOL002932 | Panicolin | 314.31 | 76.26 | 0.29 | HQ20 |
| MOL002933 | 5,7,4'-Trihydroxy-8-methoxyflavone | 300.28 | 36.56 | 0.27 | HQ21 |
| MOL002934 | NEOBAICALEIN | 374.37 | 104.34 | 0.44 | HQ22 |
| MOL002937 | DIHYDROOROXYLIN | 286.3 | 66.06 | 0.23 | HQ23 |
| MOL008206 | Moslosooflavone | 298.31 | 44.09 | 0.25 | HQ24 |
| MOL012245 | 5,7,4'-trihydroxy-6-methoxyflavanone | 302.3 | 36.63 | 0.27 | HQ25 |
| MOL012246 | 5,7,4'-trihydroxy-8-methoxyflavanone | 302.3 | 74.24 | 0.26 | HQ26 |
| MOL012266 | rivularin | 344.34 | 37.94 | 0.37 | HQ27 |
| MOL003648 | Inermin | 284.28 | 65.83 | 0.54 | RS1 |
| MOL005308 | Aposiopolamine | 271.34 | 66.65 | 0.22 | RS2 |
| MOL005317 | Deoxyharringtonine | 515.66 | 39.27 | 0.81 | RS3 |
| MOL005318 | Dianthramine | 289.26 | 40.45 | 0.2 | RS4 |
| MOL005320 | arachidonate | 304.52 | 45.57 | 0.2 | RS5 |
| MOL005321 | Frutinone A | 264.24 | 65.9 | 0.34 | RS6 |
| MOL005344 | ginsenoside rh2 | 622.98 | 36.32 | 0.56 | RS7 |
| MOL005348 | Ginsenoside-Rh4_qt | 458.8 | 31.11 | 0.78 | RS8 |
| MOL005356 | Girinimbin | 263.36 | 61.22 | 0.31 | RS9 |
| MOL005376 | Panaxadiol | 460.82 | 33.09 | 0.79 | RS10 |
| MOL005384 | suchilactone | 368.41 | 57.52 | 0.56 | RS11 |
| MOL000787 | Fumarine | 353.4 | 59.26 | 0.83 | RS12 |
| MOL003044 | Chryseriol | 300.28 | 35.85 | 0.27 | XF1 |
| MOL003542 | 8-Isopentenyl-kaempferol | 354.38 | 38.04 | 0.39 | XF2 |
| MOL004053 | Isodalbergin | 268.28 | 35.45 | 0.2 | XF3 |
| MOL004058 | Khell | 260.26 | 33.19 | 0.19 | XF4 |
| MOL010489 | Resivit | 306.29 | 30.84 | 0.27 | XF5 |
| MOL004068 | rosenonolactone | 316.48 | 79.84 | 0.37 | XF6 |
| MOL004071 | Hyndarin | 355.47 | 73.94 | 0.64 | XF7 |
| MOL004074 | stigmasterol glucoside_qt | 412.77 | 43.83 | 0.76 | XF8 |
| MOL004077 | sugeonyl acetate | 276.41 | 45.08 | 0.2 | XF9 |
| MOL000006 | luteolin | 286.25 | 36.16 | 0.25 | XF10 |
| MOL001004 | pelargonidin | 271.26 | 37.99 | 0.21 | ZB1 |
| MOL004440 | Peimisine | 427.69 | 57.4 | 0.81 | ZB2 |
| MOL004443 | Zhebeiresinol | 280.3 | 58.72 | 0.19 | ZB3 |
| MOL004446 | 6-Methoxyl-2-acetyl-3-methyl-1,4-naphthoquinone-8-O-beta-D-glucopyranoside | 422.42 | 33.31 | 0.57 | ZB4 |
| MOL002879 | Diop | 390.62 | 43.59 | 0.39 | HQ, RS |
| MOL000098 | Quercetin (A1) | 302.25 | 46.43 | 0.28 | CH, XF |
| MOL000354 | Isorhamnetin (A2) | 316.28 | 49.6 | 0.31 | CH, XF |
| MOL000359 | Sitosterol (C) | 414.79 | 36.91 | 0.75 | BS, HQ, XF |
| MOL000422 | Kaempferol (D) | 286.25 | 41.88 | 0.24 | BS, CH, RS, XF |
| MOL000449 | Stigmasterol (E) | 412.77 | 43.83 | 0.76 | HQ, CH, DG, RS, XF |

TABLE 2A-continued

| The MW, ID, OB, and DL of active compounds in Antler-Ginseng compound preparation | | | | | |
|---|---|---|---|---|---|
| MOLID | Active Ingredients | MW | OB | DL | TCM |
| MOL000358 | beta-sitosterol (B) | 414.79 | 36.91 | 0.75 | BS, HQ, DG, RS, XF, ZB |

Note:
MW (Molecule Weight), ID (identification), OB (Oral Bioavailability, and DL (Drug-likeness)

TABLE 2B

| Active Ingredients of Deer antler | | | | | | | |
|---|---|---|---|---|---|---|---|
| MOLID | Active Ingredients | MW | AlogP | Hdon | Hacc | RBN | TCM |
| MOL000041 | Phenylalanine | 165.21 | 0.96 | 3 | 3 | 3 | LJ1 |
| MOL000042 | Alanine | 89.11 | −0.6 | 3 | 3 | 1 | LJ2 |
| MOL000056 | Tyrosine | 89.11 | −0.6 | 3 | 3 | 1 | LJ3 |
| MOL000061 | Proline | 115.15 | −0.06 | 2 | 3 | 1 | LJ4 |
| MOL000067 | Valine | 117.17 | 0.24 | 3 | 3 | 2 | LJ5 |
| MOL000068 | Isoleucine | 131.2 | 0.7 | 3 | 3 | 3 | LJ6 |
| MOL000071 | Histidine | 155.18 | −1.01 | 4 | 4 | 3 | LJ7 |
| MOL001232 | Testosterone | 288.47 | 3.33 | 1 | 2 | 0 | LJ8 |
| MOL001744 | Uracil | 112.1 | −1.01 | 2 | 4 | 0 | LJ9 |
| MOL001757 | Guanine | 151.15 | −0.19 | 4 | 5 | 0 | LJ10 |
| MOL001780 | Tryptophan | 204.25 | 1.25 | 4 | 3 | 3 | LJ11 |
| MOL001831 | Hypoxanthine | 136.13 | −0.03 | 2 | 4 | 0 | LJ12 |
| MOL003969 | Serine | 105.11 | −1.49 | 4 | 4 | 2 | LJ13 |
| MOL003971 | Threonine | 119.14 | −1.11 | 4 | 4 | 2 | LJ14 |
| MOL005449 | Methionine | 149.24 | −0.27 | 3 | 3 | 4 | LJ15 |
| MOL007579 | Hydroxyproline | 131.15 | −1.15 | 3 | 4 | 1 | LJ16 |
| MOL008890 | Diethylamine | 73.16 | 0.48 | 1 | 1 | 2 | LJ17 |
| MOL009019 | (2R,3R)-3-hydroxyproline | 131.15 | −1.15 | 3 | 4 | 1 | LJ18 |
| MOL002321 | Glutamate | 129.13 | −0.67 | 2 | 4 | 1 | LJ19 |
| MOL010919 | testosterone | 288.47 | 3.33 | 1 | 2 | 0 | LJ20 |
| MOL010921 | estrone | 270.4 | 3.77 | 1 | 2 | 0 | LJ21 |
| MOL000050 | Glycine | 75.08 | −0.98 | 3 | 3 | 1 | LJ22 |

5. The Effect of Antler-Ginseng Compound Preparation on Reducing Metastasis of Tumor-Bearing Mice:

Hematoxylin-eosin (HE) staining splices of the lung in the PBS group showed multiple metastases, and the metastases in the Antler-Ginseng compound preparation group were significantly lower than the metastases in the control group.

6. The Antler-Ginseng compound preparation reduces the course of chemotherapy and the frequency of medication, and the anti-tumor effect is better than the anti-tumor effect of single-agent chemotherapy. PBS group, chemotherapy group DTX (docetaxel once a week), chemotherapy+Antler-Ginseng compound preparation (chemotherapy drugs every two weeks in combination with traditional Chinese medicine), for chemotherapy+Antler-Ginseng compound preparation, the frequency of chemotherapy drugs than chemotherapy group reduced by half.

The Antler-Ginseng compound preparation can effectively decrease the tumor weight of tumor-bearing mice, reduce the side effects of chemotherapy, and maintain the body weight of animals. The body weight of the experimental animals in the chemotherapy group was significantly reduced. The weight of chemotherapy combined with the Antler-Ginseng compound preparation treatment group was higher than the weight of the chemotherapy group and PBS group; for the tumor volume, the chemotherapy group DTX and the chemotherapy+Antler-Ginseng compound preparation group were significantly lower than the PBS group ($P<0.05$), and the chemotherapy+Antler-Ginseng compound preparation group had a lower trend than the chemotherapy group; for the tumor weight, chemotherapy group DTX and chemotherapy+Antler-Ginseng compound preparation was significantly lower than the PBS group ($P<0.05$), chemotherapy+Antler-Ginseng compound preparation group tends to lower than the chemotherapy group.

Figure 5:
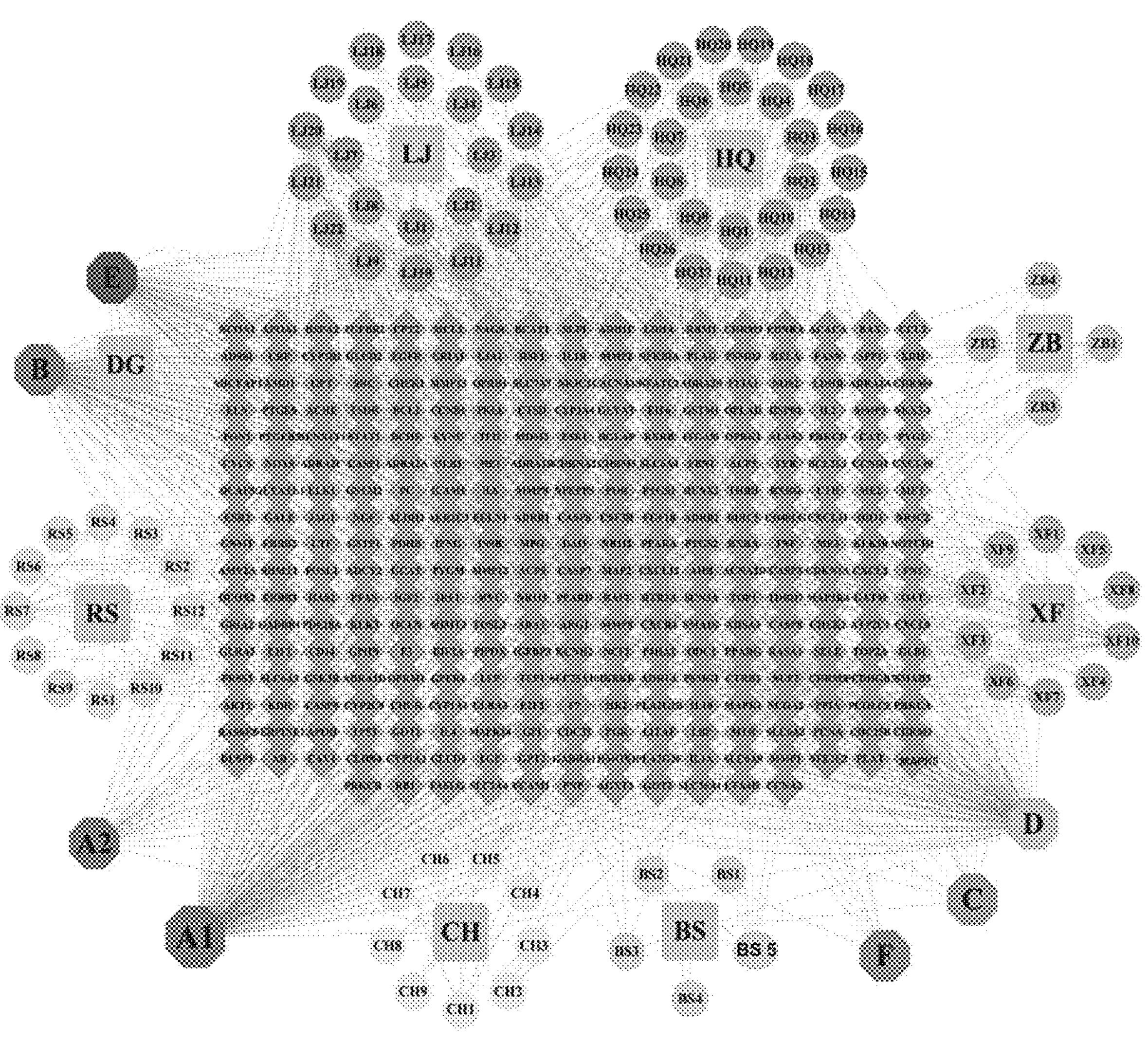
FIG. 5 is a schematic diagram of a 'drug-active ingredient-target' interaction network according to the present invention.

Network pharmacology and analysis of docking technology and protein Western blot to explore the target of Antler-Ginseng compound preparation in the treatment of breast cancer, specifically as follows:

1. Prediction of Active Ingredients and Targets of Antler-Ginseng Compound Preparation:

the active ingredients of Antler-Ginseng compound preparation were screened and the active ingredients without predicted targets and repeats were deleted, as shown in FIG. 5, a total of 96 active ingredients were obtained, meanwhile, 1776 human target proteins and 300 target genes were obtained after deleting the repeat values of the active ingredient target proteins in the TCMSP database.

Figure 6:
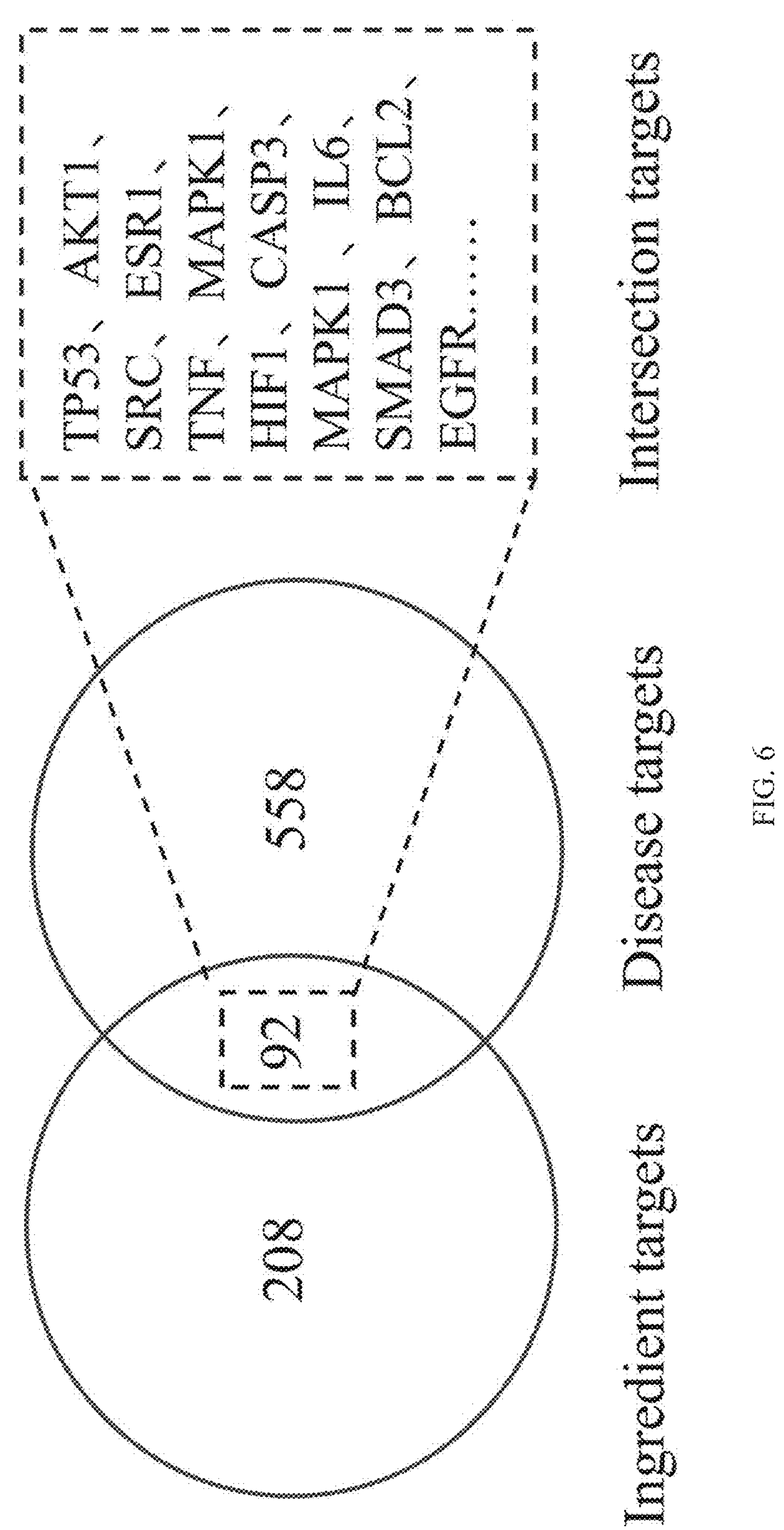
FIG. 6 is a schematic diagram of an ingredient target and a disease target Venn according to the present invention.
Figure 7:
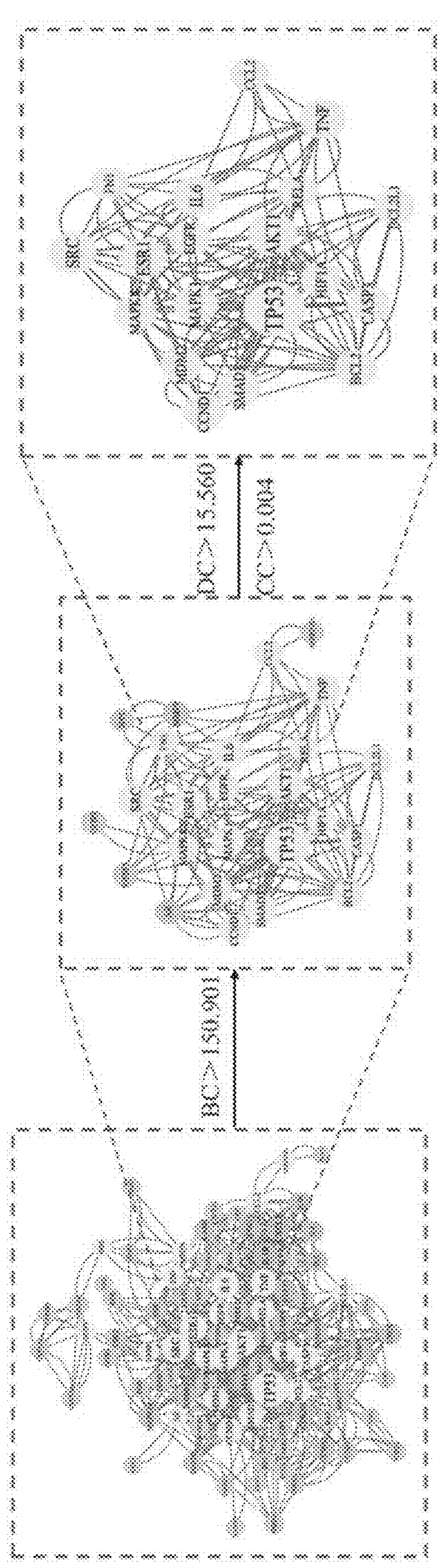
FIG. 7 is a schematic diagram of a protein-protein interaction (PPI) network topology analysis according to the present invention.
Figure 8A:
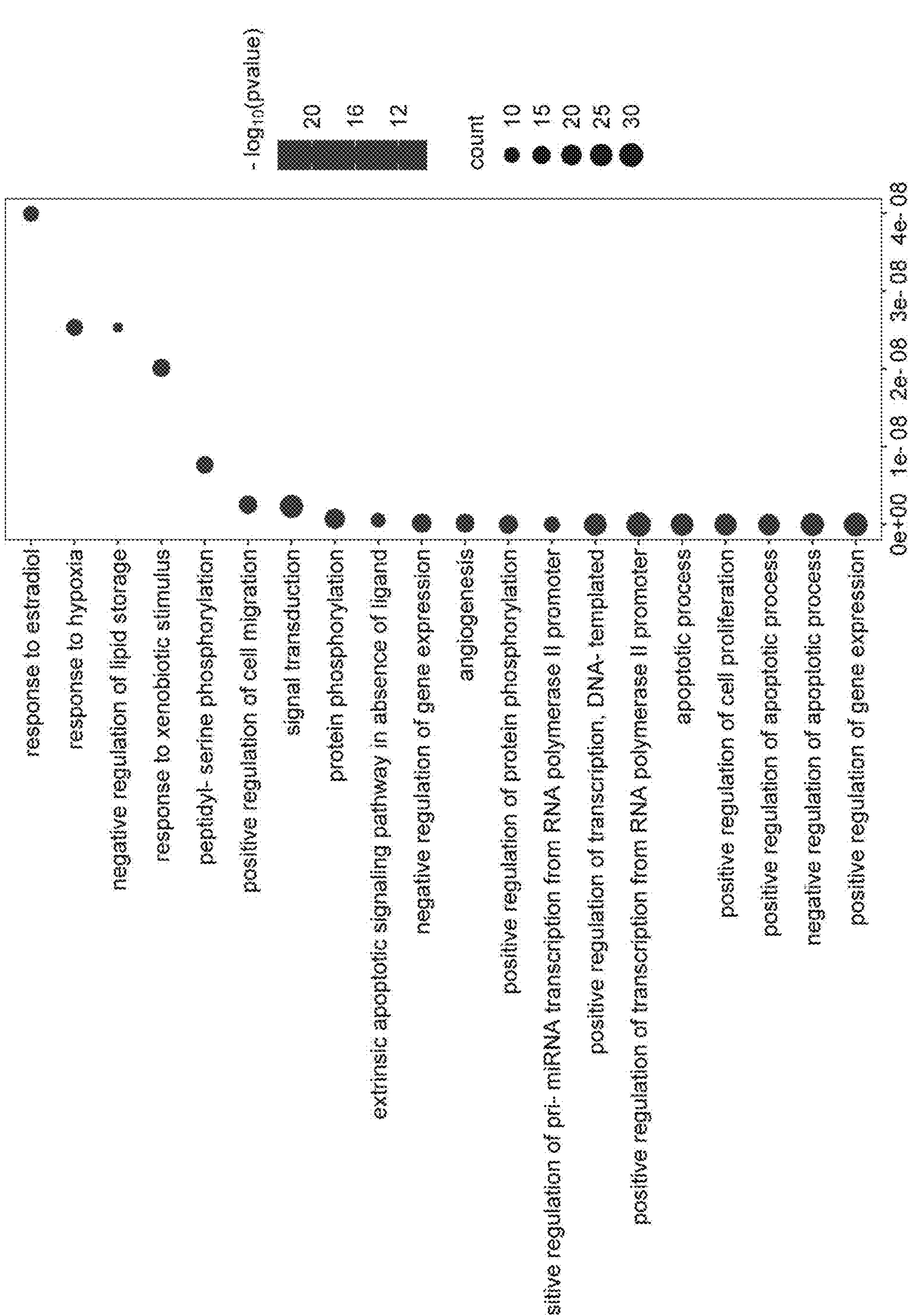
Figure 8B:
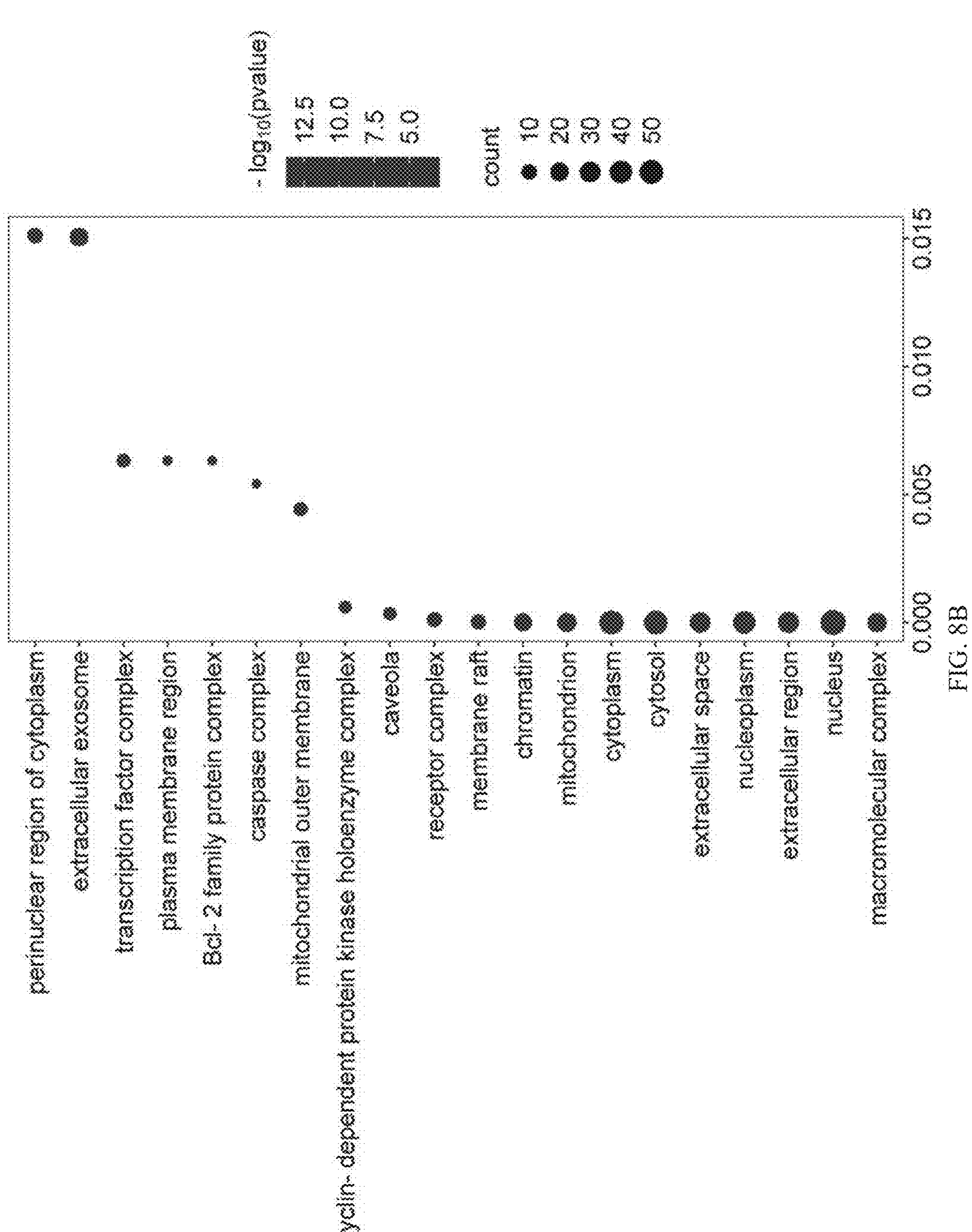
Figure 8C:
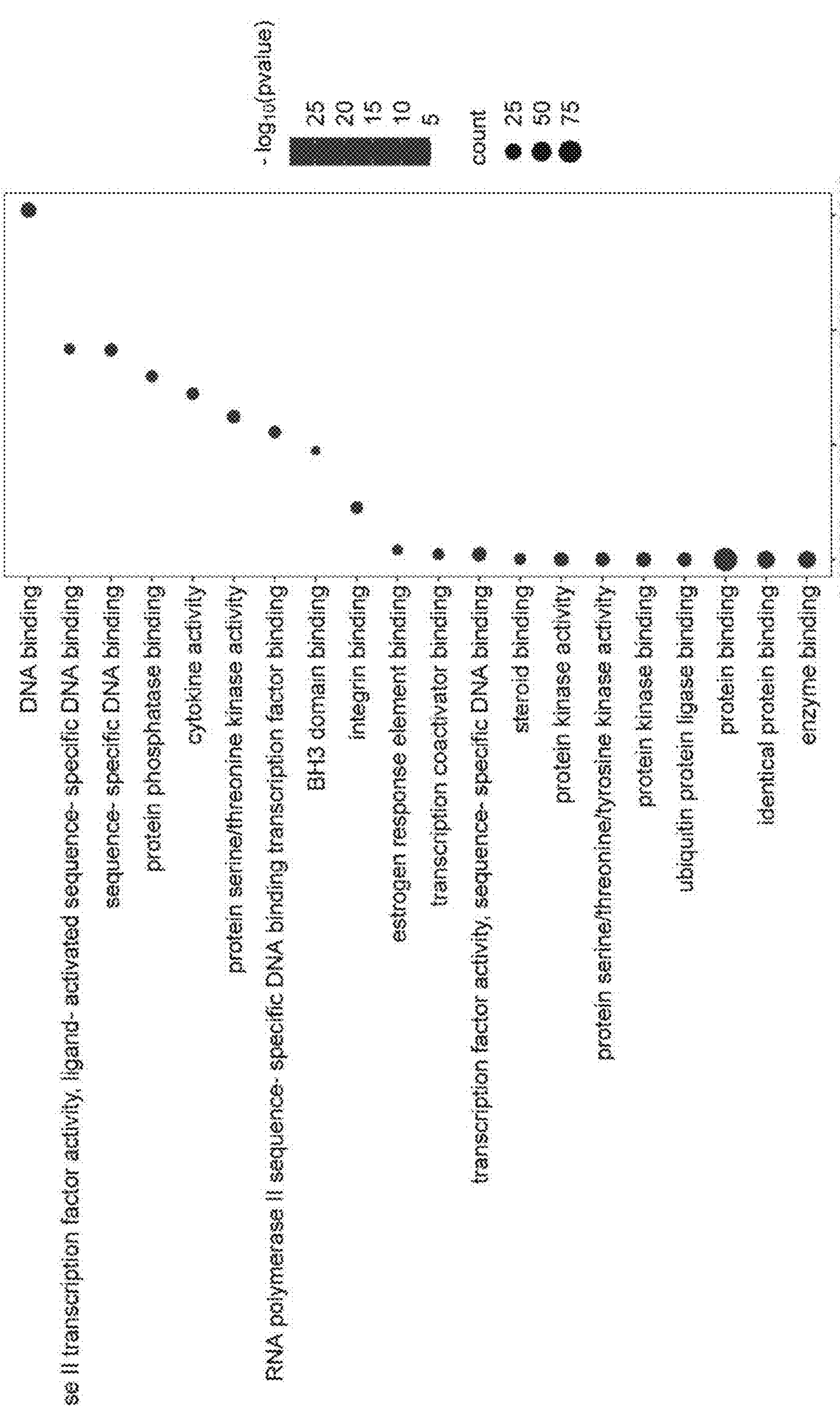
Figure 8D:
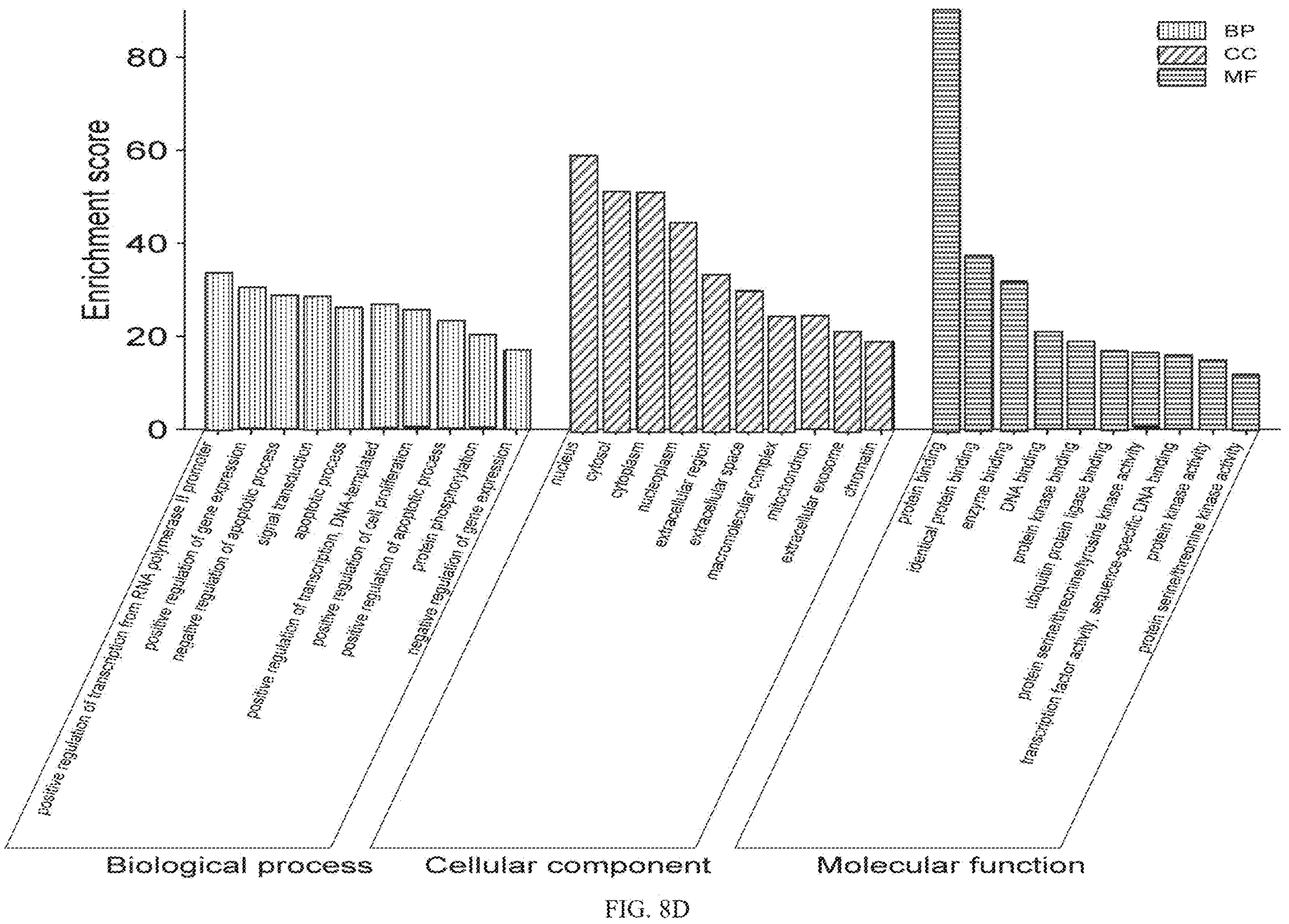
Figure 9A:
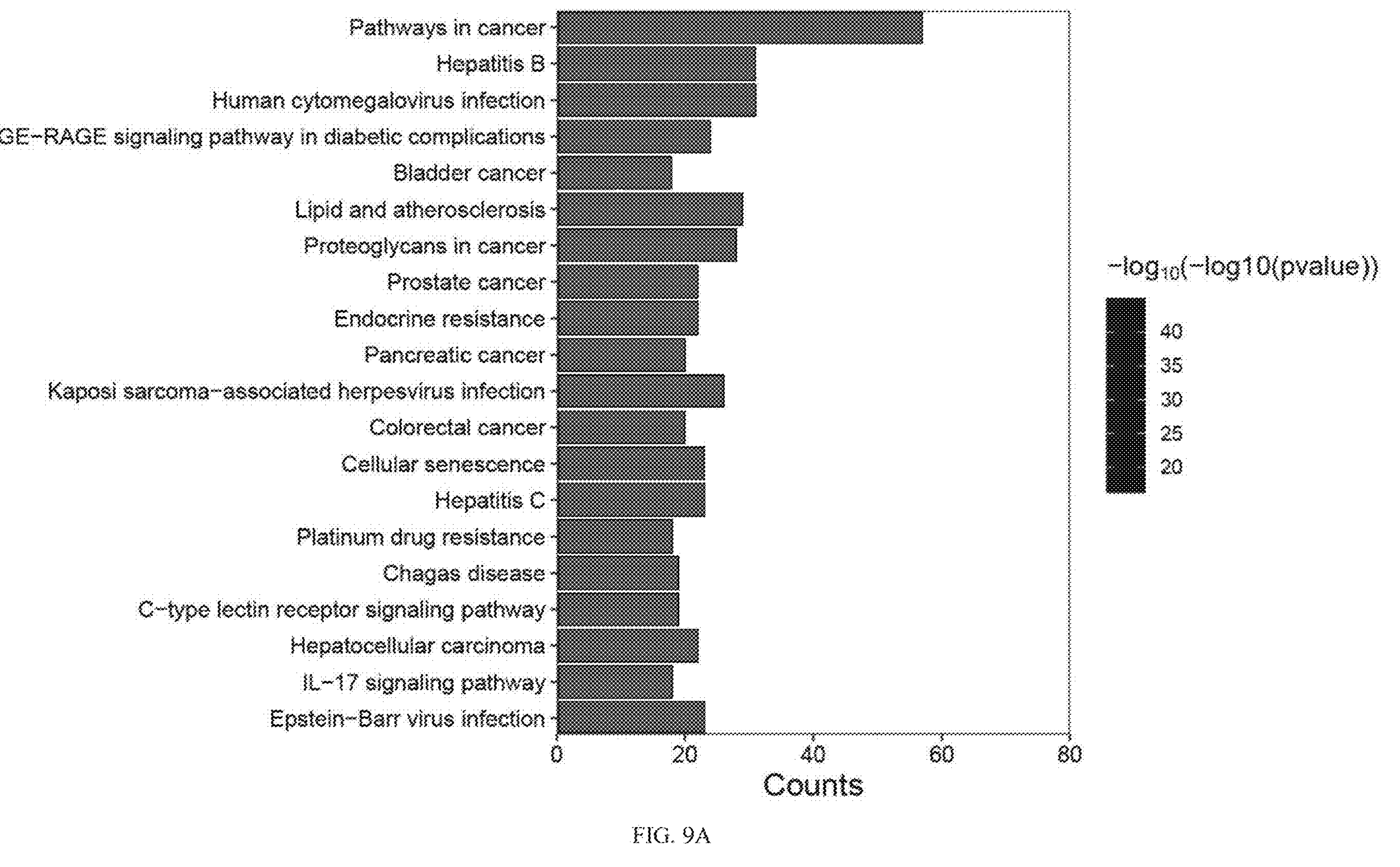
Figure 9B:
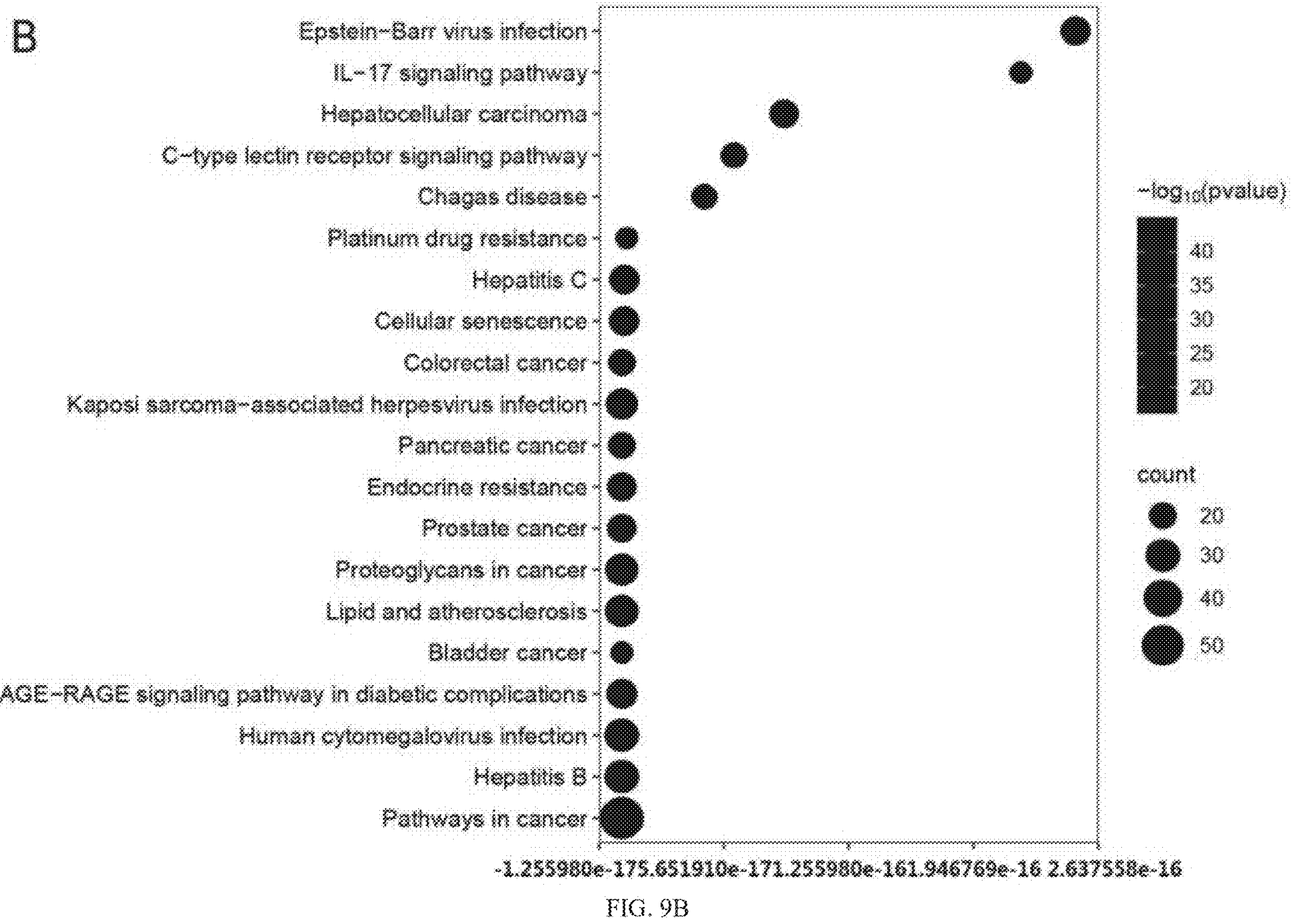
Figure 10:
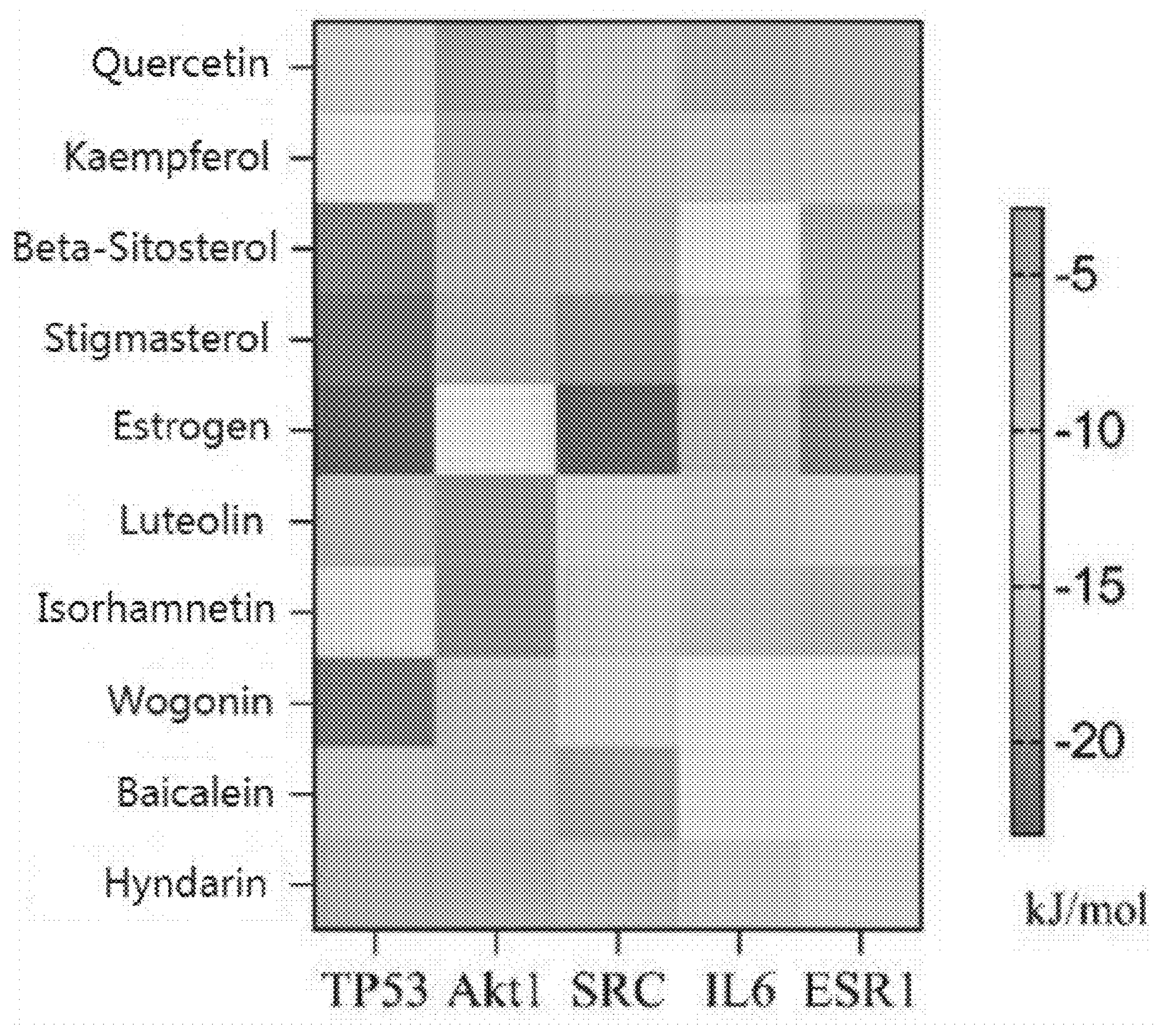
FIG. 10 is a thermal schematic of the docking of a core target with an active compound according to the present invention.

2. Targets of Breast Cancer Represented by Triple Negative:

A total of 4113 disease gene targets related to triple-negative breast cancer were obtained through the database, the median was repeatedly intercepted based on the correlation score, and 650 disease gene targets were finally obtained, which were intersected with the 300 gene targets predicted by the active ingredients of the Antler-Ginseng compound preparation by Wayne diagram, and the 92 intersection targets were finally obtained, that is, the potential target of the Antler-Ginseng compound preparation on triple-negative breast cancer, as shown in FIG. 6.

3. PPI Network Construction and Screening Results of Core Targets of 92 Intersection Targets:

The PPI network contained 92 nodes and 354 edges, and one free node was deleted, indicating that 91 targets in the network had a total of 354 interactions. The topological parameters were obtained by Cytoscape software: BC>150.901, CC>0.004, DC>15.560. Wherein 19 core targets were screened out by satisfying the three values.

Figure 11:
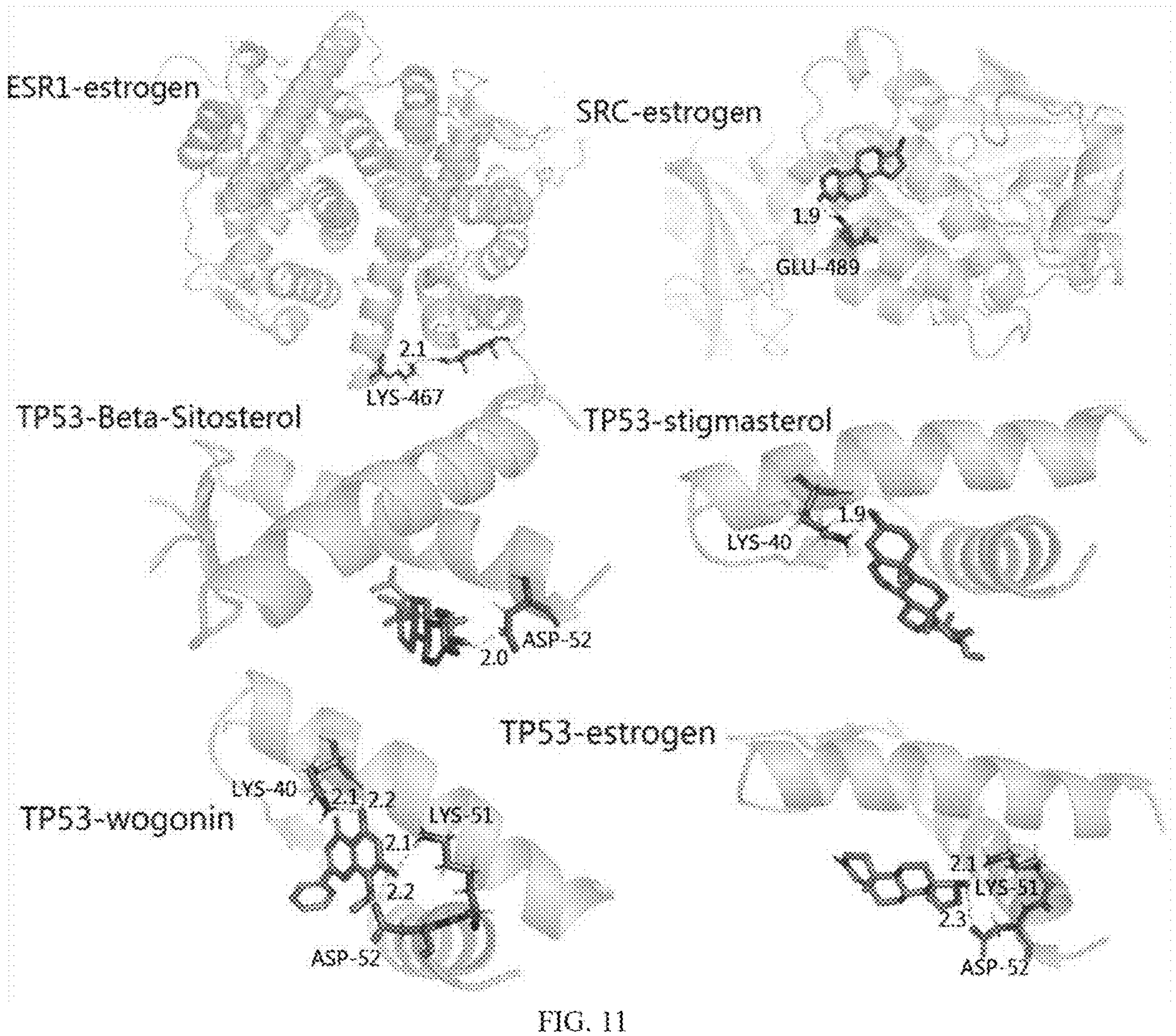
FIG. 11 is a schematic diagram of docking results of the present invention, wherein: LYS: lysine; ASP: aspartic acid; GLU: glutamic acid.

4. GO Enrichment Analysis and KEGG Pathway Annotation Analysis:

the GO functional enrichment analysis of the role of 92 targets related to the treatment of triple-negative breast cancer with Antler-Ginseng compound preparation in gene function is shown in FIG. 11. There were 530 BP-related items, mainly involving positive regulation of gene expression, negative regulation of apoptosis process, signal transduction, positive regulation of cell proliferation, protein autophosphorylation, negative regulation of gene expression, etc.; there were 120 Molecular Function (MF)-related items, mainly involving protein binding, enzyme binding, DNA binding, protein kinase binding, ubiquitin protein ligase binding, protein serine/threonine/tyrosine kinase activity transcription factor activity, sequence-specific DNA binding, etc.; there are 56 CC-related items, mainly involving nucleus, cytoplasm, nucleoplasm, macromolecular complex, mitochondria, exosomes, chromatin, etc.

The enrichment function of the KEGG pathway was used to explore the role of 92 potential gene targets in the signaling pathway of Antler-Ginseng compound preparation in the treatment of triple-negative breast cancer. The enrichment results showed that there were 160 related pathways, the top 20 enrichment pathways were screened based on the FDR value and P value, as shown in FIG. 11, and the most prominent pathway was the cancer pathway.

5. Molecular Docking Results:

according to the degree value, the top 10 main active drug ingredients were screened, and the molecular docking verification results were carried out with the top 5 targets among the 19 core targets, and the docking results were evaluated by docking binding energy, as shown in Table 3. The docking score heat map between the core target and the active compound was drawn, as shown in FIG. 11, the top 6 with good docking results were visualized, and the docking had a good active pocket structure, as shown in FIG. 11, through the visual analysis of molecular docking results, it can be seen that different active ingredients and target protein receptors are better combined by hydrogen bonds. There were 47 with docking binding energy≤−5 KJ/mol, indicating that the main active ingredients of Antler-Ginseng compound preparations for the treatment of triple-negative breast cancer can be closely combined with the corresponding target proteins, and have good binding energy, so as to play a pharmacodynamic role. In addition, the results of molecular docking showed that the docking targets were mainly closely related to the cancer pathway, such as TP53, AKT1, SRC, IL6, ESR1, etc., mainly involving oncogenes, tumor suppressor genes, signal transduction, tumor immunity, chromosome mutation and other issues, which is further proved that the active ingredients of Antler-Ginseng compound preparation can interfere with the occurrence and development of triple-negative breast cancer by acting on cancer-related targets and related signaling pathways.

TABLE 3

Molecular docking results (unit: kJ/mol)

| Source | Active ingredients | TP53 | AKT1 | SRC | IL6 | ESR1 |
|---|---|---|---|---|---|---|
| A1 | Quercetin | −14.98 | −4.31 | −9.12 | −6.57 | −7.03 |
| D | Kaempferol | −13.14 | −6.69 | −8.7 | −9.29 | −9.58 |
| B | Beta-Sitosterol | −20.33 | −7.11 | −16.32 | −12.18 | −17.44 |
| E | Stigmasterol | −21.80 | −6.32 | −19.04 | −14.85 | −17.44 |
| LJ20 | Estrogen | −22.97 | −13.18 | −22.89 | −16.53 | −20.37 |
| XF10 | Luteolin | −16.57 | −3.56 | −10.38 | −9.41 | −9.87 |
| A2 | Isorhamnetin | −13.68 | −2.87 | −9.5 | −8.45 | −7.49 |
| HQ2 | Wogonin | −20.96 | −7.94 | −14.39 | −12.47 | −12.72 |
| HQ9 | Baicalein | −15.52 | −7.78 | −17.53 | −12.26 | −12.55 |
| XF7 | Hyndarin | −16.82 | −6.86 | −15.98 | −14.94 | −14.18 |

Figure 12A:
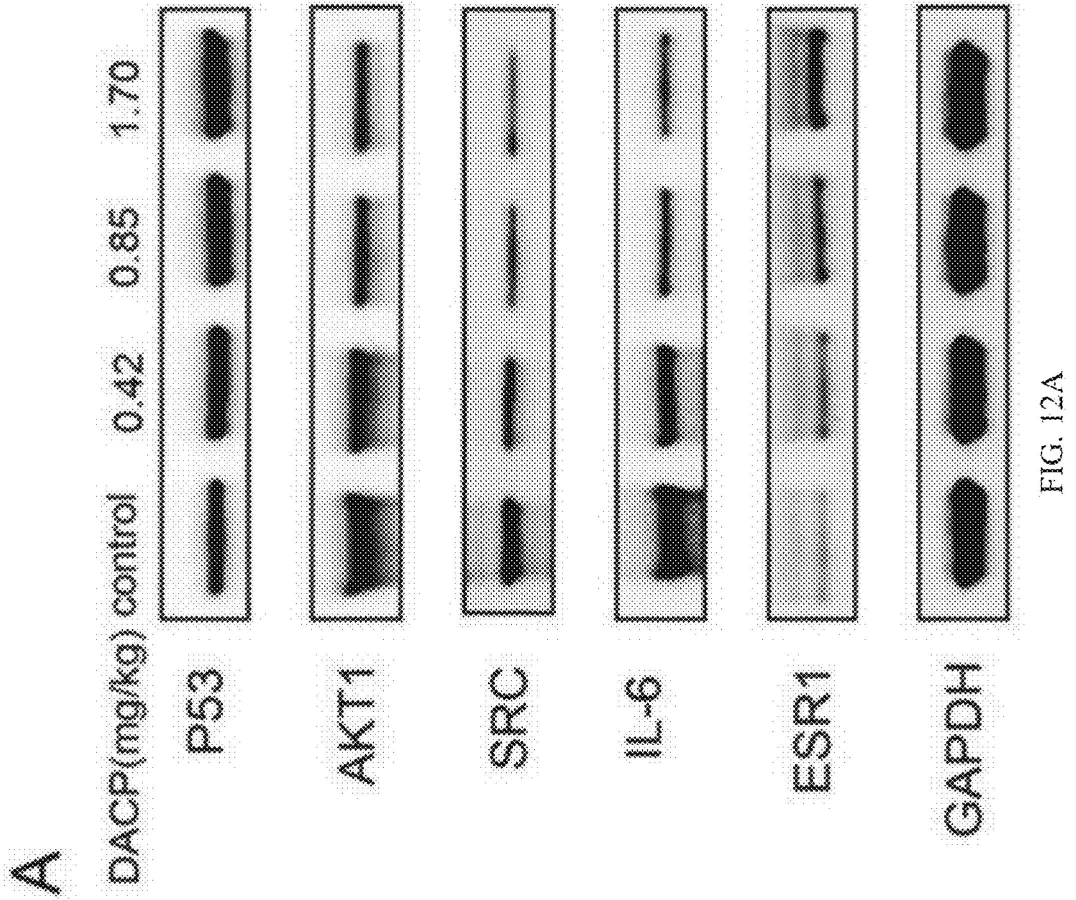
FIGS. 12A-12B are schematic diagrams of an Antler-Ginseng compound preparation for reducing oncogene expression and increasing tumor suppressor gene expression confirmed by western blot according to the present invention.
Figure 12B:
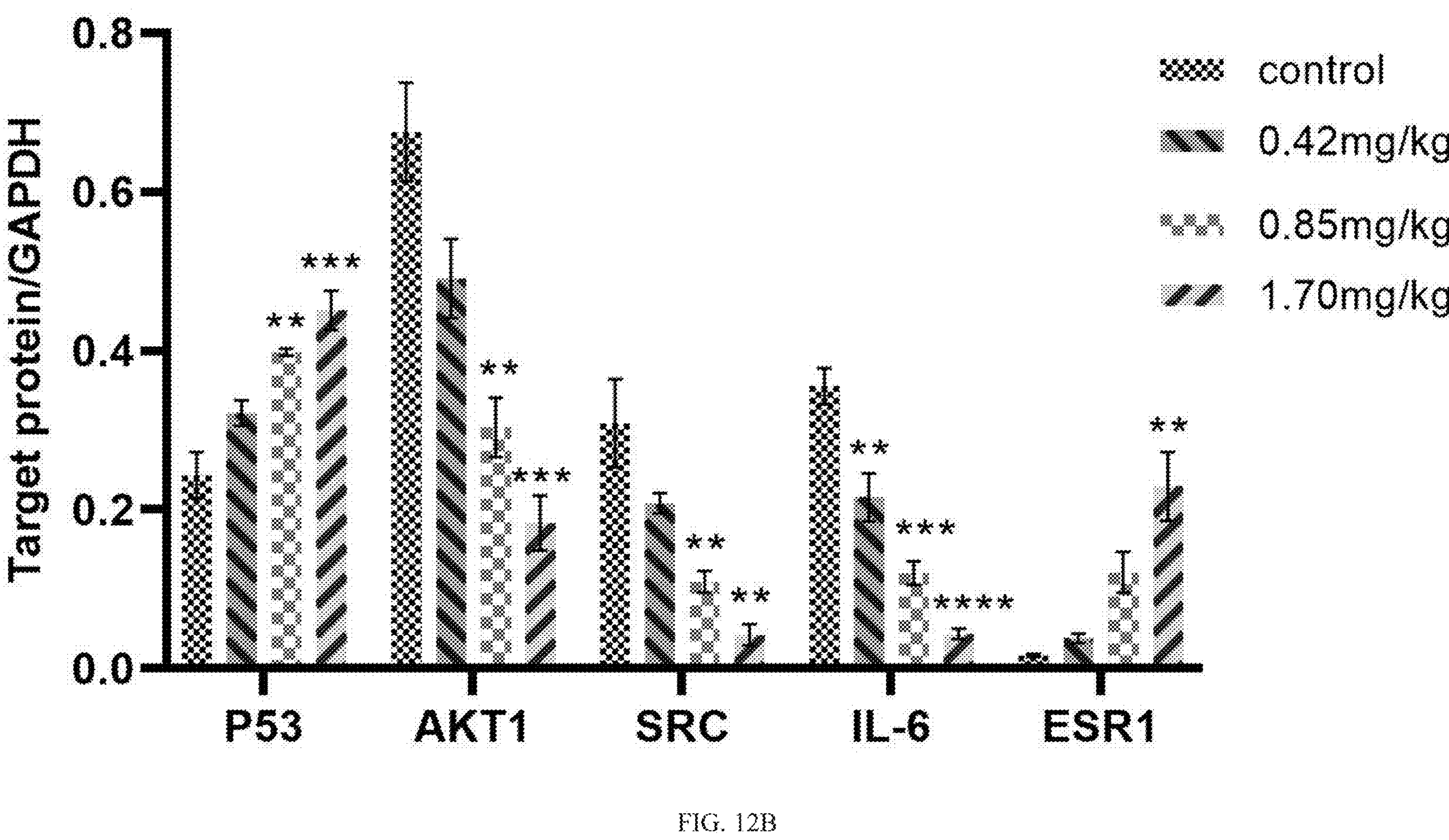

6. Molecular verification of Western Blot: the Antler-Ginseng compound preparation inhibits breast cancer by inhibiting oncogenes or cancer-promoting factors AKT, IL-6, and SRC, and by enhancing the expression of tumor suppressor gene P53, as shown in FIG. 11 and FIGS. 12A-12B.

Figure 13:
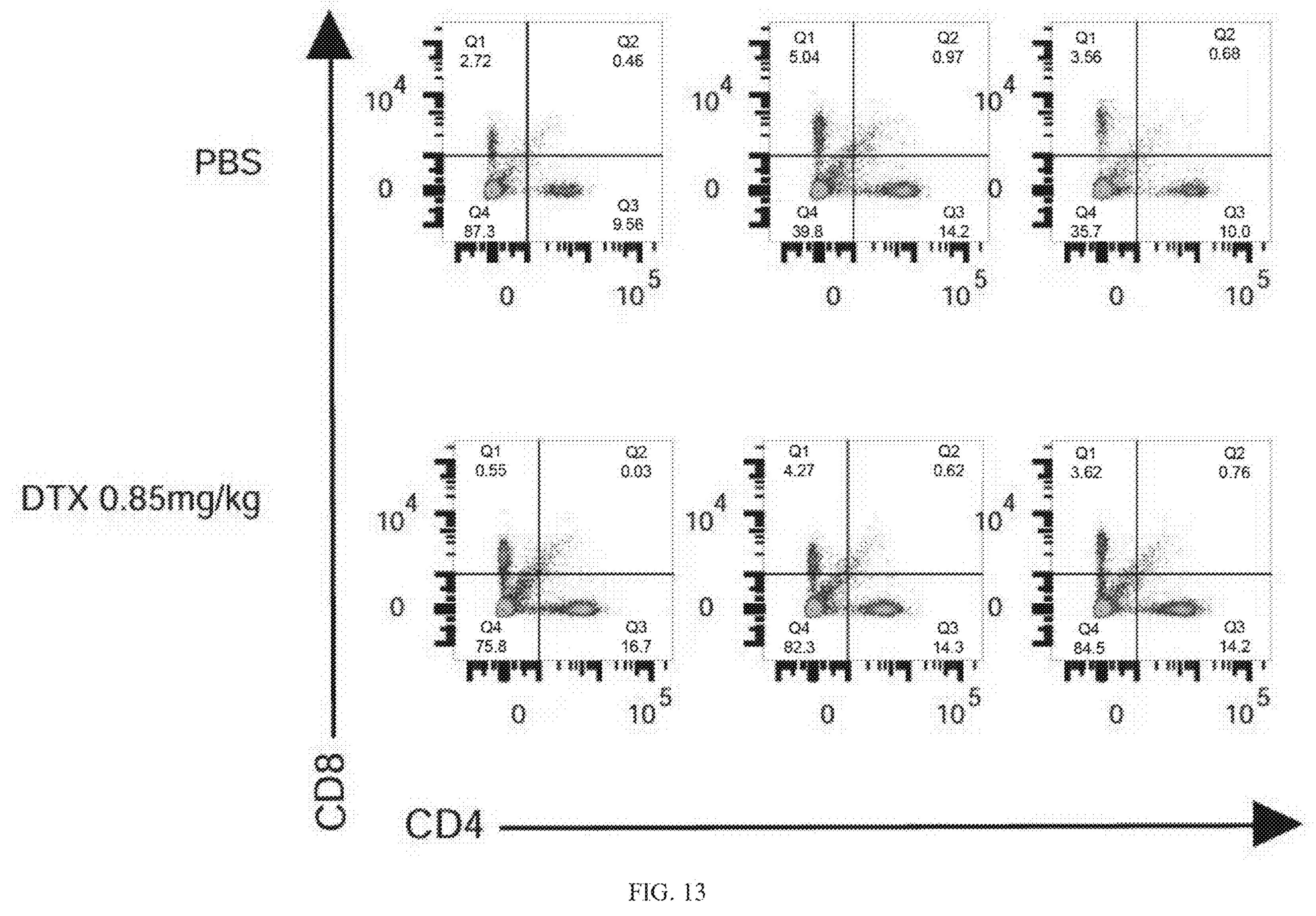
FIG. 13 is a schematic diagram of ability of an Antler-Ginseng compound preparation to enhance immune cells according to the present invention.

7. Effect of Antler-Ginseng compound preparation on immune ability: Antler-Ginseng compound preparation can improve the helper T cells (CD4) and killer T cells (CD8) of tumor-bearing mice, as shown in FIG. 13.

What is claimed is:

1. A drug for a treatment of a breast cancer, comprising antler and ginseng as a sovereign drug, wherein the drug is made of the antler and the ginseng as the sovereign drug, angelicae sinensis radix and radix paeoniae alba as an adjuvant drug, and combined with radix bupleuri, scutellariae radix, cyperi rhizoma, and thunberg fritillary bulb; wherein the drug, in parts by weight, comprises: 12 parts of the antler, 3 parts of the ginseng, 10 parts of the angelicae sinensis radix, 10 parts of the radix paeoniae alba, 5 parts of the radix bupleuri, 5 parts of the scutellariae radix, 10 parts of the cyperi rhizoma, and 10 parts of the thunberg fritillary bulb.

2. A preparation method of the drug for the treatment of the breast cancer according to claim 1, comprising:

step 1, taking 12 parts by weight of the antler and 3 parts by weight of the ginseng and soaking separately to obtain a soaked antler and a soaked ginseng;

step 2, taking 10 parts by weight of the angelicae sinensis radix, 10 parts by weight of the radix paeoniae alba, 5 parts by weight of the radix bupleuri, 5 parts by weight of the scutellariae radix, 10 parts by weight of the cyperi rhizoma, and 10 parts by weight of the thunberg fritillary bulb, and adding water of 8 times a total weight of the angelicae sinensis radix, the radix paeoniae alba, the radix bupleuri, the scutellariae radix, the cyperi rhizoma, and the thunberg fritillary bulb to fully immerse to obtain a soaked angelicae sinensis radix, a soaked radix paeoniae alba, a soaked radix bupleuri, a soaked scutellariae radix, a soaked cyperi rhizoma, a soaked thunberg fritillary bulb, and a soaking solution;

step 3, decocting 12 parts of the soaked antler in the step 1 for 0.5 h, then adding 10 parts of the soaked angelicae sinensis radix, 10 parts of the soaked radix paeoniae alba, 5 parts of the soaked radix bupleuri, 5 parts of the soaked scutellariae radix, 10 parts of the soaked cyperi rhizoma, 10 parts of the soaked thunberg fritillary bulb, and the soaking solution, and continuing to decoct to obtain a decocted pharmaceutical decoction;

step 4, separately decocting 3 parts of the soaked ginseng in the step 1 to obtain a decocted ginseng aqueous solution, and adding the decocted ginseng aqueous solution into the decocted pharmaceutical decoction in the step 3 to obtain a mixture; and decocting the mixture for 3 times, 2 h each time, filtering by a gauze to obtain an intermediate filtrate and combining the intermediate filtrate for 3 times to obtain a final filtrate; and step 5, compressing the final filtrate obtained in the step 4 to a paste by a rotary evaporator under a reduced pressure, placing the paste in a freeze dryer, pre-freezing at −20° C. for 12 h, sublimation-drying at a room temperature for 24 h, then placing in a vacuum dryer for 48 h, after a completion of drying, turning off a vacuum pump, collecting a dry powder sample, and sealing and storing the dry powder sample at −20° C. for a future use.

* * * * *